(12) United States Patent
Zhang et al.

(10) Patent No.: US 11,920,137 B2
(45) Date of Patent: Mar. 5, 2024

(54) PRODUCTION OF CAROTENOIDS AND APOCAROTENOIDS

(71) Applicant: AGENCY FOR SCIENCE, TECHNOLOGY AND RESEARCH, Singapore (SG)

(72) Inventors: Congqiang Zhang, Singapore (SG); Xixian Chen, Singapore (SG); Heng-Phon Too, Singapore (SG)

(73) Assignee: AGENCY FOR SCIENCE, TECHNOLOGY AND RESEARCH, Singapore (SG)

( * ) Notice: Subject to any disclaimer, the term of this patent is extended or adjusted under 35 U.S.C. 154(b) by 868 days.

(21) Appl. No.: 16/488,504

(22) PCT Filed: Feb. 26, 2018

(86) PCT No.: PCT/SG2018/050087
§ 371 (c)(1),
(2) Date: Aug. 23, 2019

(87) PCT Pub. No.: WO2018/156086
PCT Pub. Date: Aug. 30, 2018

(65) Prior Publication Data
US 2019/0367928 A1    Dec. 5, 2019

(30) Foreign Application Priority Data
Feb. 24, 2017 (SG) .......................... 10201701500U

(51) Int. Cl.
| | | |
|---|---|---|
| *C12N 15/52* | (2006.01) | |
| *C12N 9/02* | (2006.01) | |
| *C12N 9/90* | (2006.01) | |
| *C12N 15/62* | (2006.01) | |
| *C12N 15/70* | (2006.01) | |
| *C12P 5/02* | (2006.01) | |
| *C12P 7/26* | (2006.01) | |
| *C12P 23/00* | (2006.01) | |

(52) U.S. Cl.
CPC ............ *C12N 15/52* (2013.01); *C12N 9/0069* (2013.01); *C12N 9/90* (2013.01); *C12N 15/62* (2013.01); *C12N 15/70* (2013.01); *C12P 5/026* (2013.01); *C12P 7/26* (2013.01); *C12P 23/00* (2013.01); *C12Y 113/11063* (2015.07); *C12Y 113/11068* (2015.07); *C12Y 505/01018* (2013.01); *C12Y 505/01019* (2013.01)

(58) Field of Classification Search
CPC ........ C12N 15/52; C12N 9/0069; C12N 9/90; C12N 15/62; C12N 15/70; C12P 5/026; C12P 7/26; C12P 23/00; C12Y 113/11063; C12Y 113/11068; C12Y 505/01018; C12Y 505/01019; C12Y 113/11051; C07K 14/245
See application file for complete search history.

(56) References Cited

U.S. PATENT DOCUMENTS

| | | | |
|---|---|---|---|
| 10,364,434 B2 * | 7/2019 | Wang | ..................... C12N 9/001 |
| 2003/0087337 A1 | 5/2003 | Giraud et al. | |
| 2004/0219629 A1 | 11/2004 | Cheng et al. | |
| 2009/0175911 A1 | 7/2009 | Cutting et al. | |
| 2009/0178156 A1 | 7/2009 | Tanksley et al. | |
| 2018/0251796 A1 | 9/2018 | Jack et al. | |

FOREIGN PATENT DOCUMENTS

| | | |
|---|---|---|
| WO | WO-2016/154314 A1 | 9/2016 |
| WO | WO-2017/036495 A1 | 3/2017 |

OTHER PUBLICATIONS

Zhang et al. Experimental design-aided systematic pathway optimization of glucose uptake and deoxyxylulose phosphate pathway for improved amorphadiene production Appl Microbiol Biotechnol (2015) 99:3825-3837 (Year: 2015).*
Daniela S. Floss Role of carotenoid cleavage dioxygenase 1 (CCD1) in apocarotenoid biogenesis revisited [Plant Signaling & Behavior 4:3, 172-175; Mar. 2009] (Year: 2009).*
Communication Pursuant to Article 94(3) EPC in EP Application No. 18758451.1 dated Jan. 18, 2022, 5 pages.
Invitation to Respond to Written Opinion with Written Opinion in SG Application No. 11201907812T dated Feb. 22, 2022, 10 pages.
Zhu et al., "Targeted Engineering and Scale Up of Lycopene Overproduction in *Escherichia coli*", Process Biochemistry, vol. 50, No. 3, Dec. 27, 2014, pp. 341-346.
Lu et al., "Laboratory-Scale Production of $^{13}$C-Labeled Lycopene and Phytoene by Bioengineered *Escherichia coli*", J. Agric Food Chem, vol. 59, No. 18, Sep. 2, 2011, pp. 9996-10005.
Ahrazem et al., "The Carotenoid Cleavage Dioxygenase CCD2 Catalysing the Synthesis of Crocetin in Spring Crocuses and Saffron is a Plastidial Enzyme", New Phytol, vol. 209, No. 2, Sep. 17, 2015, pp. 650-663.
Huang et al., "Cloning and Functional Characterization of Carotenoid Cleavage Dioxygenase 4 Genes", Journal of Experimental Botany, vol. 60, No. 11, May 12, 2009, pp. 3011-3022.
Baldermann et al., "Functional Characterizatin of a Carotenoid Cleavage Dioxygenase 1 and its Relation to the Carotenoid Accumulation and Volatile Emission During the Floral Development of *Osmanthus fragrans* Lour", Journal of Experimental Botany, vol. 61, No. 11, May 17, 2010, pp. 2967-2977.
Cunningham et al., "One Ring or Two? Determination of Ring Number in Carotenoids by Lycopene ε-cyclases", Proc Natl Acad Sci U.S.A., vol. 9 8, No. 5, Feb. 27, 2011, pp. 2905-2910.

(Continued)

*Primary Examiner* — Ganapathirama Raghu
(74) *Attorney, Agent, or Firm* — MARSHALL, GERSTEIN & BORUN LLP

(57) ABSTRACT

A method for producing a carotenoid or apocarotenoid is disclosed. The method comprises the step of expressing in a host cell an expression module comprising an expression vector having a coding region encoding at least one optimised carotenoid or apocarotenoid generating enzyme, the coding region being operably linked to a promoter. A host cell comprising an expression vector having a coding region encoding at least one optimised carotenoid or apocarotenoid generating enzyme, the coding region being operably linked to a promoter is also provided together with a kit.

14 Claims, 22 Drawing Sheets
Specification includes a Sequence Listing.

(56) References Cited

OTHER PUBLICATIONS

Zhang et al., "Experimental Design-aided Systematic Pathway Optimization of Glucose Uptake and Deoxyxylulose Phosphate Pathway for Improved Amorphadiene Production", Appl Microbiol Biotechnol, vol. 99, No. 9, Feb. 26, 2015, pp. 3825-3837.

Zhang et al., "A "plug-n-play" Modular Metabolic System for the Production of Apocarotenoids", Biotechnol Bioeng, vol. 115, No. 1, Oct. 27, 2017, pp. 174-183.

G. Armstrong, "Eubacteria Show Their True Colors: Genetics of Carotenoid Pigment Biosynthesis From Microbes to Plants", Journal of Bacteriology, vol. 176, No. 16, Aug. 1994, pp. 4795-4802.

Jang et al., "Retinoid Production Using Metabolically Engineered *Escherichia coli* With a Two-phase Culture System", Microbial Cell Factories, 10:59, 2011, 12 pages.

López et al., "Production of β-ionone by Combined Expression of Carotenogenic and Plant CCD1 Genes in *Saccharomyces cerevisiae*", Microbial Cell Factories, 14:84, 2015, 13 pages.

Search Report and Written Opinion in International Application No. PCT/SG2018/050087 dated May 16, 2018, 17 pages.

Extended European Search Report in EP Application No. 18758451.1 dated Apr. 15, 2021, 17 pages.

Cunningham et al., "A Portfolio of Plasmids for Identification and Analysis of Carotenoid Pathway Enzymes: *Adonis aestivalis* as a Case Study", Photosynth Research. vol. 92, No. 2, Jul. 17, 2007, pp. 245-259.

Liao et al., "The Potential of the Mevalonate Pathway for Enhanced Isoprenoid Production", Biotechnology Advances, vol. 34, No. 5, Mar. 16, 2016, pp. 697-713.

Chen et al., "Integrating Enzyme and Metabolic Engineering Tools for Enhanced α-Ionone Production", Journal of Agricultural and Food Chemistry, vol. 67, No. 49, Dec. 11, 2019, pp. 13451-13459.

Seo et al., "Molecular Cloning and Co-Expression of Phytoene Synthase Gene from *Kocuria gwangalliensis* in *Escherichia coli*", Journal of Microbiology and Biotechnology, vol. 25, No. 11, Nov. 28, 2015, pp. 1801-1809.

Seo et al., "Molecular Cloning and Co-Expression of Phytoene Synthase Gene from *Kocuria gwangalliensis* in *Escherichia coli*", J. Microbiol. Biotechnol., vol. 25, No. 11, 2015, pp. 1801-1809.

Liao et al., "The Potential of the Mevalonate Pathway for Enhanced Isoprenoid Production", Biotechnology Advances, vol. 34, 2016, pp. 697-713.

Invitation to Respond to Written Opinion with Written Opinion in SG Application No. 11201907812T dated Oct. 19, 2020, 10 pages.

Search Report in EP Application No. 18758451.1 dated Nov. 30, 2020, 16 pages.

Communication Pursuant to Article 94(3) EPC in Application No. 18758451.1, dated Aug. 1, 2022, 4 pages.

First Office Action issued in Chinese Patent Application No. 201880026537.1, dated Aug. 8, 2022, 18 pages including English translation.

Second Office Action in CN Application No. 2018800265371 dated Jan. 19, 2023, 27 pages.

Communication Pursuant to Article 94(3) EPC in Application No. 18758451.1 dated Feb. 21, 2023, 4 pages.

\* cited by examiner

FIG. 6
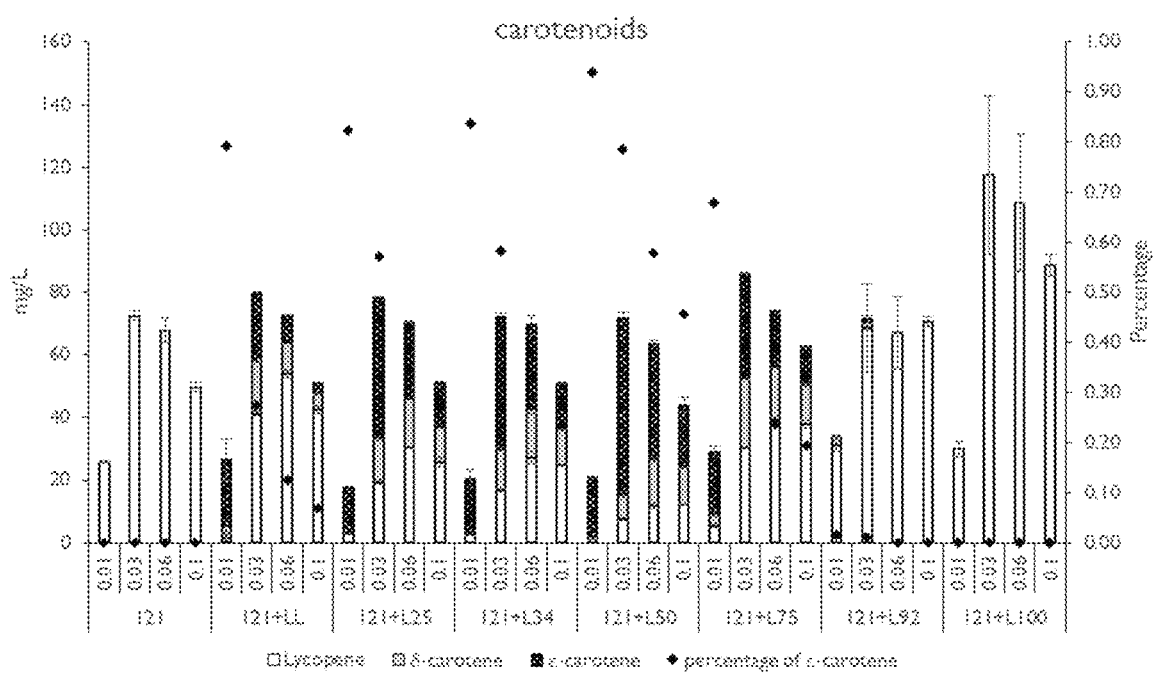
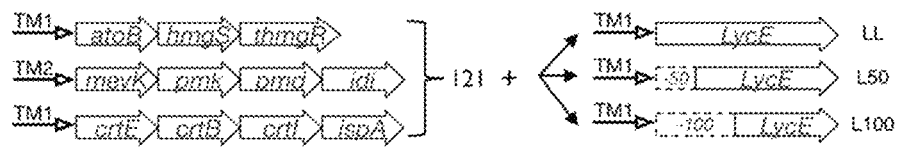

FIG. 15
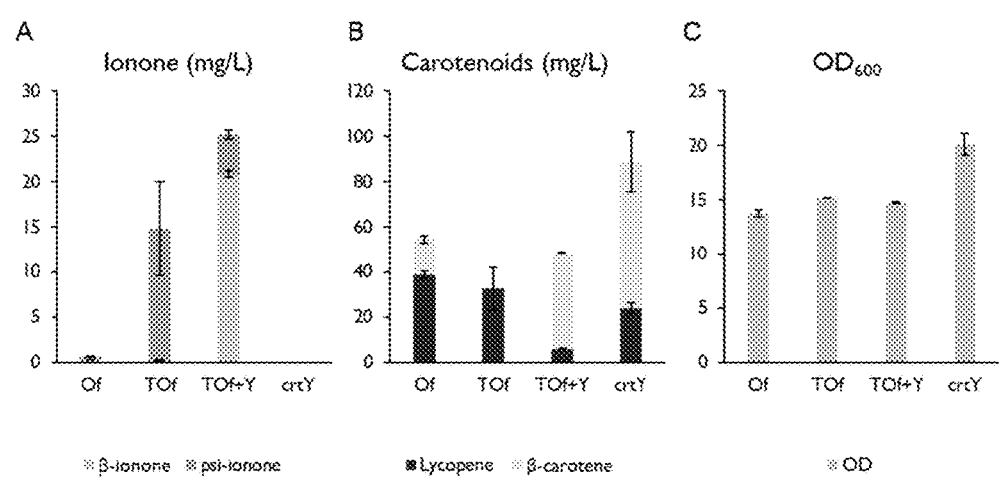
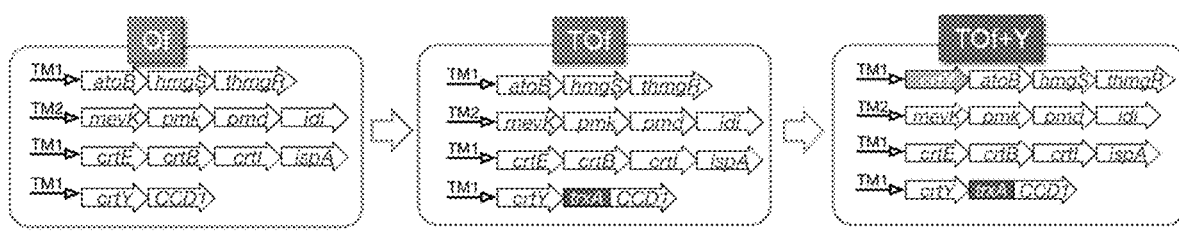

FIG. 18

```
sp|O65572|CCD1_ARATH      ------MAEKLSDGSSIISVHPRPSKGFSSKLLDLLERLVVKLMHDASLPHYLSGNFAP    54
tr|Q6E4P3|Q6E4P3_PETHY    MGRKESDDGVERIEGGVVVVNPKPKKGITAKAIDLLEKVIIKLMHDSSKPLHYLSGNFAP    60
tr|U3M7F6|U3M7F6_VITVI    --MAE---KEEQGGAGVAVVDPKPSKGFTSKAVDWLEKLIVKLMYDSSQPLHYLSGNFAP    55
tr|D4QE74|D4QE74_9LAMI    MGMQG---EDAQRTGNIVAVKPKPSQGLTSKAIDWLEWLFVKMMHDSKQPLHYLSGNFAP    57
                                   ..:  *.*:*.:*:::*  :*  **  :.:*:*:*:. ********** sp|O65572|CCD1_ARATH      IRDETPPVKDLPVHGFLPECLNGEFVRVGPNPKFDAVAGYHWFDGDGMIHGVRIKDGKAT   114
tr|Q6E4P3|Q6E4P3_PETHY    T-DETPPLNDLPIKGHLPECLNGEFVRVGPNPKFAPVAGYHWFDGDGMIHGLRIKDGKAT   119
tr|U3M7F6|U3M7F6_VITVI    VRDETPPCKNLPVIGYLPECLNGEFVRVGPNPKFSPVAGYHWFDGDGMIHGLHIKDGKAT   115
tr|D4QE74|D4QE74_9LAMI    V-DETPPLKDLPVTGHLPECLNGEFVRVGPNPKFASIAGYHWFDGDGMIHGMRIKDGKAT   116
                            **  ::: * .***************  :*********::***** sp|O65572|CCD1_ARATH      YVSRYVKTSRLKQEEFFGAAKFMKIGDLKGFFGLLMVNVQQLRTKLKILDNTYGNGTANT   174
tr|Q6E4P3|Q6E4P3_PETHY    YVSRYVRTSRLKQEEFFEGAKFMKIGDLKGLFGLFTVYMQMLRAKLKILDTSYGNGTANT   179
tr|U3M7F6|U3M7F6_VITVI    YVSRYVRTSRLKQEEYFGGAKFMRIGDLKGLFGLLMVNMQMLRAKLKILDVSYGTGTGNT   175
tr|D4QE74|D4QE74_9LAMI    YVSRYVQTSRLKQEEFFGRAMFMKIGDLKGMFGLLMVNMQMLRAKLKVLDISYGIGTANT   176
                          ******:*******:* *   * **:******:***:  * :* **:***:**  :** **.**

sp|O65572|CCD1_ARATH      ALVYHHGKLLALQEADKPYVIKVLEDGDLQTLGIIDYDKRLTHSFTAHPKVDPVTGEMFT   234
tr|Q6E4P3|Q6E4P3_PETHY    ALVYHHGKLLALSEADKPYALKVLEDGDLQTLGMLDYDKRLLHSFTAHPKVDPVTGEMFT   239
tr|U3M7F6|U3M7F6_VITVI    ALVFHRGKLLALSEADKPYVLKVLEDGDLQTLGMLDYDKRLTHSFTAHPKVDPFTGEMFS   235
tr|D4QE74|D4QE74_9LAMI    ALVYHHGKLLALSEADKPYAIKVLEDGDLQTIGLLDYDKRLAHSFTAHPKVDPFTGEMFT   236
                          ***:*:****** ****** :**********:*::******  *************.*****:

sp|O65572|CCD1_ARATH      FGYSHTPPYLTYRVISKDGIMHDPVPITISEPIMMHDFAITETYAIFMDLPMHFRPKEMV   294
tr|Q6E4P3|Q6E4P3_PETHY    FGYAHEPPYITYRVISKDGIMQDPVPITIPEAIMMHDFAITENYAIMMDLPLCFRPKEMV   299
tr|U3M7F6|U3M7F6_VITVI    FGYSHTPPYITYRVISKDGFMHEPVPITISDPIMMHDFAITENYAIFMDLPLYFRPKEMV   295
tr|D4QE74|D4QE74_9LAMI    FGYSHTPPYVTYRVISKDGAMNDPVPITVSGPIMMHDFAITENYAIFMDLPLYFKPKEMV   296
                          ***:* *:******* *:*****: .* ********.:*** *:***** sp|O65572|CCD1_ARATH      KEKKMIYSFDPTKKARFGVLPRYAKDELMIRWFELPNCFIFHNANAWEEEDEVVLITCRL   354
tr|Q6E4P3|Q6E4P3_PETHY    KNNQLAFTFDTTKKARFGVLPRYAKSEALIRWFELPNCFIFHNANAWEEEDEVVLITCRL   359
tr|U3M7F6|U3M7F6_VITVI    KEKKLIFTFDATKKARFGVLPRYAKNELHIKWFELPNCFIFHNANAWEEGDEVVLITCRL   355
tr|D4QE74|D4QE74_9LAMI    KDKKFIFSFDATQKARFGILPRYAKNELLIKWFELPNCFIFHNANAWEEGDEVVLITCRL   356
                          *:::: ::** *::*** :**: *  *:***************  ******** sp|O65572|CCD1_ARATH      ENPDLDMVSGKVKEKLENFGNELYEMRFNMKTGSASQKKLSASAVDFPRINECYTGKKQR   414
tr|Q6E4P3|Q6E4P3_PETHY    PHPDLDMVNGEVKENLENFSNELYEMRFNMKSGAASQKKLSESSVDFPRINENYTGRKQR   419
tr|U3M7F6|U3M7F6_VITVI    EHPDLDLVGGDVKEKLENFGNELYEMRFNMKTGIASQRKLSASSVDFPRVNESYTGRKQR   415
tr|D4QE74|D4QE74_9LAMI    ENPDLDMVNSTVKERLDNFKNELYEMRFNLQNGLASQKKLSVSAVDFPRVNESYTTRKQR   416
                          :.****:*..  ***.*: *******:.. *:*:* :* **:..* .:* sp|O65572|CCD1_ARATH      YVYGTILDSIAKVTGIIKFDLHAEAETGKRMLEVGGNIKGIYDLGEGRYGSEAIYVPRE-   473
tr|Q6E4P3|Q6E4P3_PETHY    YVYGTTLNSIAKVTGIIKFDLHAEPETGKKQLEVGGNVQGIFDLGPGRFGSEAVFVPSQP   479
tr|U3M7F6|U3M7F6_VITVI    YVYGTILDSIAKVTGIIKFDLHAEPDTGKSKLEVGGNVQGIFDLGVGRFGSEAVFVPREP   475
tr|D4QE74|D4QE74_9LAMI    YVYGTTLDKIAKVTGIIKFDLHAEPETGKEKLELGGNVKGIFDLGPGRFGSEAVFVPRHP   476
                          *****  *::***************  :***  **:***::**:*** **:****::**   .

sp|O65572|CCD1_ARATH      --TAEEDDGYLIFFVHDENTGKSCVTVIDAKTMSAEPVAVVELPHRVPYGFHALFVTEEQ   531
tr|Q6E4P3|Q6E4P3_PETHY    GTECEEDDGYLIFFVHDENTGKSAVNVIDAKTMSAEPVAVVELPKRVPYGFHAFFVTEEQ   539
tr|U3M7F6|U3M7F6_VITVI    GITSEEDDGYLIFFVHDEKTGKSYVNVIDAKTMSPDPIAIVELPNRVPYGFHAFFVTEEQ   535
tr|D4QE74|D4QE74_9LAMI    GITSEEDDGYLIFFVHDENTGKSAVNVIDAKTMSPDPVAVVELPKRVPYGFHAFFVTEDQ   536
                            .*******::*****:***  *:*********  :*:*:*****:.*:********:*******:

sp|O65572|CCD1_ARATH      LQEQTLI    538    SEQ ID NO: 5
tr|Q6E4P3|Q6E4P3_PETHY    IQEQAKL    546    SEQ ID NO: 8
tr|U3M7F6|U3M7F6_VITVI    LKEQAKL    542    SEQ ID NO: 6
tr|D4QE74|D4QE74_9LAMI    LQEQAKV    543    SEQ ID NO: 7
                          ::**: :
```

FIG. 21
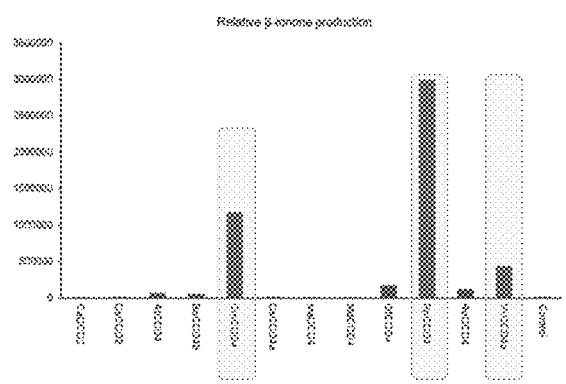
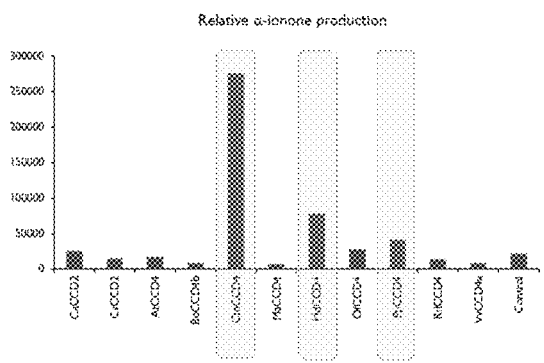

SEQUENCE LISTING

<160> NUMBER OF SEQ ID NOS: 8

<210> SEQ ID NO 1
<211> LENGTH: 32
<212> TYPE: DNA
<213> ORGANISM: Bacteriophage T7

<400> SEQUENCE: 1
taatacgact cactataggg gaattgtgag cg             32

<210> SEQ ID NO 2
<211> LENGTH: 32
<212> TYPE: DNA
<213> ORGANISM: Artificial Sequence
<220> FEATURE:
<223> OTHER INFORMATION: TM1 promoter

<400> SEQUENCE: 2
taatacgact cactaatggg gaattgtgag cg             32

<210> SEQ ID NO 3
<211> LENGTH: 32
<212> TYPE: DNA
<213> ORGANISM: Artificial Sequence
<220> FEATURE:
<223> OTHER INFORMATION: TM2 promoter

<400> SEQUENCE: 3
taatacgact cactcgaggg gaattgtgag cg             32

-continued

```
<210> SEQ ID NO 4
<211> LENGTH: 32
<212> TYPE: DNA
<213> ORGANISM: Artificial Sequence
<220> FEATURE:
<223> OTHER INFORMATION: TM3 promoter

<400> SEQUENCE: 4
taatacgact cactataaag gaattgtgag cg                                     32

<210> SEQ ID NO 5
<211> LENGTH: 538
<212> TYPE: PRT
<213> ORGANISM: Arabidopsis thaliana

<400> SEQUENCE: 5
```

Met Ala Glu Lys Leu Ser Asp Gly Ser Ser Ile Ile Ser Val His Pro
1               5                   10                  15

Arg Pro Ser Lys Gly Phe Ser Ser Lys Leu Leu Asp Leu Leu Glu Arg
            20                  25                  30

Leu Val Val Lys Leu Met His Asp Ala Ser Leu Pro Leu His Tyr Leu
        35                  40                  45

Ser Gly Asn Phe Ala Pro Ile Arg Asp Glu Thr Pro Pro Val Lys Asp
    50                  55                  60

Leu Pro Val His Gly Phe Leu Pro Glu Cys Leu Asn Gly Glu Phe Val
65                  70                  75                  80

Arg Val Gly Pro Asn Pro Lys Phe Asp Ala Val Ala Gly Tyr His Trp
                85                  90                  95

Phe Asp Gly Asp Gly Met Ile His Gly Val Arg Ile Lys Asp Gly Lys
            100                 105                 110

Ala Thr Tyr Val Ser Arg Tyr Val Lys Thr Ser Arg Leu Lys Gln Glu
        115                 120                 125

Glu Phe Phe Gly Ala Ala Lys Phe Met Lys Ile Gly Asp Leu Lys Gly
    130                 135                 140

Phe Phe Gly Leu Leu Met Val Asn Val Gln Gln Leu Arg Thr Lys Leu
145                 150                 155                 160

Lys Ile Leu Asp Asn Thr Tyr Gly Asn Gly Thr Ala Asn Thr Ala Leu
                165                 170                 175

Val Tyr His His Gly Lys Leu Leu Ala Leu Gln Glu Ala Asp Lys Pro
            180                 185                 190

Tyr Val Ile Lys Val Leu Glu Asp Gly Asp Leu Gln Thr Leu Gly Ile
        195                 200                 205

Ile Asp Tyr Asp Lys Arg Leu Thr His Ser Phe Thr Ala His Pro Lys
    210                 215                 220

Val Asp Pro Val Thr Gly Glu Met Phe Thr Phe Gly Tyr Ser His Thr
225                 230                 235                 240

Pro Pro Tyr Leu Thr Tyr Arg Val Ile Ser Lys Asp Gly Ile Met His
                245                 250                 255

Asp Pro Val Pro Ile Thr Ile Ser Glu Pro Ile Met Met His Asp Phe
            260                 265                 270

Ala Ile Thr Glu Thr Tyr Ala Ile Phe Met Asp Leu Pro Met His Phe
        275                 280                 285

Arg Pro Lys Glu Met Val Lys Glu Lys Met Ile Tyr Ser Phe Asp
    290                 295                 300

Pro Thr Lys Lys Ala Arg Phe Gly Val Leu Pro Arg Tyr Ala Lys Asp
305                 310                 315                 320

-continued

```
Glu Leu Met Ile Arg Trp Phe Glu Leu Pro Asn Cys Phe Ile Phe His
                325                 330                 335

Asn Ala Asn Ala Trp Glu Glu Asp Glu Val Val Leu Ile Thr Cys
            340                 345                 350

Arg Leu Glu Asn Pro Asp Leu Asp Met Val Ser Gly Lys Val Lys Glu
            355                 360                 365

Lys Leu Glu Asn Phe Gly Asn Glu Leu Tyr Glu Met Arg Phe Asn Met
        370                 375                 380

Lys Thr Gly Ser Ala Ser Gln Lys Lys Leu Ala Ser Ala Val Asp
385                 390                 395                 400

Phe Pro Arg Ile Asn Glu Cys Tyr Thr Gly Lys Lys Gln Arg Tyr Val
                405                 410                 415

Tyr Gly Thr Ile Leu Asp Ser Ile Ala Lys Val Thr Gly Ile Ile Lys
                420                 425                 430

Phe Asp Leu His Ala Glu Ala Glu Thr Gly Lys Arg Met Leu Glu Val
            435                 440                 445

Gly Gly Asn Ile Lys Gly Ile Tyr Asp Leu Gly Glu Gly Arg Tyr Gly
        450                 455                 460

Ser Glu Ala Ile Tyr Val Pro Arg Glu Thr Ala Glu Glu Asp Asp Gly
465                 470                 475                 480

Tyr Leu Ile Phe Phe Val His Asp Glu Asn Thr Gly Lys Ser Cys Val
                485                 490                 495

Thr Val Ile Asp Ala Lys Thr Met Ser Ala Glu Pro Val Ala Val Val
                500                 505                 510

Glu Leu Pro His Arg Val Pro Tyr Gly Phe His Ala Leu Phe Val Thr
            515                 520                 525

Glu Glu Gln Leu Gln Glu Gln Thr Leu Ile
        530                 535

<210> SEQ ID NO 6
<211> LENGTH: 542
<212> TYPE: PRT
<213> ORGANISM: Vitis vinifera

<400> SEQUENCE: 6

Met Ala Glu Lys Glu Glu Gln Gly Gly Ala Gly Val Ala Val Val Asp
1               5                   10                  15

Pro Lys Pro Ser Lys Gly Phe Thr Ser Lys Ala Val Asp Trp Leu Glu
                20                  25                  30

Lys Leu Ile Val Lys Leu Met Tyr Asp Ser Ser Gln Pro Leu His Tyr
            35                  40                  45

Leu Ser Gly Asn Phe Ala Pro Val Arg Asp Glu Thr Pro Pro Cys Lys
        50                  55                  60

Asn Leu Pro Val Ile Gly Tyr Leu Pro Glu Cys Leu Asn Gly Glu Phe
65                  70                  75                  80

Val Arg Val Gly Pro Asn Pro Lys Phe Ser Pro Val Ala Gly Tyr His
                85                  90                  95

Trp Phe Asp Gly Asp Gly Met Ile His Gly Leu His Ile Lys Asp Gly
                100                 105                 110

Lys Ala Thr Tyr Val Ser Arg Tyr Val Arg Thr Ser Arg Leu Lys Gln
            115                 120                 125

Glu Glu Tyr Phe Gly Gly Ala Lys Phe Met Arg Ile Gly Asp Leu Lys
        130                 135                 140

Gly Leu Phe Gly Leu Leu Met Val Asn Met Gln Met Leu Arg Ala Lys
145                 150                 155                 160
```

```
Leu Lys Ile Leu Asp Val Ser Tyr Gly Thr Gly Asn Thr Ala
            165                 170                 175

Leu Val Phe His Arg Gly Lys Leu Leu Ala Leu Ser Glu Ala Asp Lys
            180                 185                 190

Pro Tyr Val Leu Lys Val Leu Glu Asp Gly Asp Leu Gln Thr Leu Gly
            195                 200                 205

Met Leu Asp Tyr Asp Lys Arg Leu Thr His Ser Phe Thr Ala His Pro
            210                 215                 220

Lys Val Asp Pro Phe Thr Gly Glu Met Phe Ser Phe Gly Tyr Ser His
225                 230                 235                 240

Thr Pro Pro Tyr Ile Thr Tyr Arg Val Ile Ser Lys Asp Gly Phe Met
            245                 250                 255

His Glu Pro Val Pro Ile Thr Ile Ser Asp Pro Ile Met Met His Asp
            260                 265                 270

Phe Ala Ile Thr Glu Asn Tyr Ala Ile Phe Met Asp Leu Pro Leu Tyr
            275                 280                 285

Phe Arg Pro Lys Glu Met Val Lys Glu Lys Leu Ile Phe Thr Phe
            290                 295                 300

Asp Ala Thr Lys Lys Ala Arg Phe Gly Val Leu Pro Arg Tyr Ala Lys
305                 310                 315                 320

Asn Glu Leu His Ile Lys Trp Phe Glu Leu Pro Asn Cys Phe Ile Phe
            325                 330                 335

His Asn Ala Asn Ala Trp Glu Glu Asp Glu Val Val Leu Ile Thr
            340                 345                 350

Cys Arg Leu Glu His Pro Asp Leu Asp Leu Val Gly Gly Asp Val Lys
            355                 360                 365

Glu Lys Leu Glu Asn Phe Gly Asn Glu Leu Tyr Glu Met Arg Phe Asn
            370                 375                 380

Met Lys Thr Gly Ile Ala Ser Gln Arg Lys Leu Ser Ala Ser Ser Val
385                 390                 395                 400

Asp Phe Pro Arg Val Asn Glu Ser Tyr Thr Gly Arg Lys Gln Arg Tyr
            405                 410                 415

Val Tyr Gly Thr Ile Leu Asp Ser Ile Ala Lys Val Thr Gly Ile Ile
            420                 425                 430

Lys Phe Asp Leu His Ala Glu Pro Asp Thr Gly Lys Ser Lys Leu Glu
            435                 440                 445

Val Gly Gly Asn Val Gln Gly Ile Phe Asp Leu Gly Val Gly Arg Phe
            450                 455                 460

Gly Ser Glu Ala Val Phe Val Pro Arg Glu Pro Gly Ile Thr Ser Glu
465                 470                 475                 480

Glu Asp Asp Gly Tyr Leu Ile Phe Phe Val His Asp Glu Lys Thr Gly
            485                 490                 495

Lys Ser Tyr Val Asn Val Ile Asp Ala Lys Thr Met Ser Pro Asp Pro
            500                 505                 510

Ile Ala Ile Val Glu Leu Pro Asn Arg Val Pro Tyr Gly Phe His Ala
            515                 520                 525

Phe Phe Val Thr Glu Glu Gln Leu Lys Glu Gln Ala Lys Leu
            530                 535                 540

<210> SEQ ID NO 7
<211> LENGTH: 543
<212> TYPE: PRT
<213> ORGANISM: Osmanthus fragrans
```

```
<400> SEQUENCE: 7

Met Gly Met Gln Gly Glu Asp Ala Gln Arg Thr Gly Asn Ile Val Ala
1               5                   10                  15

Val Lys Pro Lys Pro Ser Gln Gly Leu Thr Ser Lys Ala Ile Asp Trp
            20                  25                  30

Leu Glu Trp Leu Phe Val Lys Met Met His Asp Ser Lys Gln Pro Leu
        35                  40                  45

His Tyr Leu Ser Gly Asn Phe Ala Pro Val Asp Glu Thr Pro Pro Leu
    50                  55                  60

Lys Asp Leu Pro Val Thr Gly His Leu Pro Glu Cys Leu Asn Gly Glu
65                  70                  75                  80

Phe Val Arg Val Gly Pro Asn Pro Lys Phe Ala Ser Ile Ala Gly Tyr
                85                  90                  95

His Trp Phe Asp Gly Asp Gly Met Ile His Gly Met Arg Ile Lys Asp
            100                 105                 110

Gly Lys Ala Thr Tyr Val Ser Arg Tyr Val Gln Thr Ser Arg Leu Lys
        115                 120                 125

Gln Glu Glu Phe Phe Gly Arg Ala Met Phe Met Lys Ile Gly Asp Leu
    130                 135                 140

Lys Gly Met Phe Gly Leu Leu Met Val Asn Met Gln Met Leu Arg Ala
145                 150                 155                 160

Lys Leu Lys Val Leu Asp Ile Ser Tyr Gly Ile Gly Thr Ala Asn Thr
                165                 170                 175

Ala Leu Val Tyr His His Gly Lys Leu Leu Ala Leu Ser Glu Ala Asp
            180                 185                 190

Lys Pro Tyr Ala Ile Lys Val Leu Glu Asp Gly Asp Leu Gln Thr Ile
        195                 200                 205

Gly Leu Leu Asp Tyr Asp Lys Arg Leu Ala His Ser Phe Thr Ala His
    210                 215                 220

Pro Lys Val Asp Pro Phe Thr Gly Glu Met Phe Thr Phe Gly Tyr Ser
225                 230                 235                 240

His Thr Pro Pro Tyr Val Thr Tyr Arg Val Ile Ser Lys Asp Gly Ala
                245                 250                 255

Met Asn Asp Pro Val Pro Ile Thr Val Ser Gly Pro Ile Met Met His
            260                 265                 270

Asp Phe Ala Ile Thr Glu Asn Tyr Ala Ile Phe Met Asp Leu Pro Leu
        275                 280                 285

Tyr Phe Lys Pro Lys Glu Met Val Lys Asp Lys Lys Phe Ile Phe Ser
    290                 295                 300

Phe Asp Ala Thr Gln Lys Ala Arg Phe Gly Ile Leu Pro Arg Tyr Ala
305                 310                 315                 320

Lys Asn Glu Leu Leu Ile Lys Trp Phe Glu Leu Pro Asn Cys Phe Ile
                325                 330                 335

Phe His Asn Ala Asn Ala Trp Glu Glu Gly Asp Glu Val Val Leu Ile
            340                 345                 350

Thr Cys Arg Leu Glu Asn Pro Asp Leu Asp Met Val Asn Ser Thr Val
        355                 360                 365

Lys Glu Arg Leu Asp Asn Phe Lys Asn Glu Leu Tyr Glu Met Arg Phe
    370                 375                 380

Asn Leu Gln Asn Gly Leu Ala Ser Gln Lys Lys Leu Ser Val Ser Ala
385                 390                 395                 400

Val Asp Phe Pro Arg Val Asn Glu Ser Tyr Thr Thr Arg Lys Gln Arg
                405                 410                 415
```

```
Tyr Val Tyr Gly Thr Thr Leu Asp Lys Ile Ala Lys Val Thr Gly Ile
                420                 425                 430

Ile Lys Phe Asp Leu His Ala Glu Pro Glu Thr Gly Lys Glu Lys Leu
        435                 440                 445

Glu Leu Gly Gly Asn Val Lys Gly Ile Phe Asp Leu Gly Pro Gly Arg
    450                 455                 460

Phe Gly Ser Glu Ala Val Phe Val Pro Arg His Pro Gly Ile Thr Ser
465                 470                 475                 480

Glu Glu Asp Asp Gly Tyr Leu Ile Phe Phe Val His Asp Glu Asn Thr
                485                 490                 495

Gly Lys Ser Ala Val Asn Val Ile Asp Ala Lys Thr Met Ser Pro Asp
                500                 505                 510

Pro Val Ala Val Val Glu Leu Pro Lys Arg Val Pro Tyr Gly Phe His
                515                 520                 525

Ala Phe Phe Val Thr Glu Asp Gln Leu Gln Glu Gln Ala Lys Val
                530                 535                 540

<210> SEQ ID NO 8
<211> LENGTH: 546
<212> TYPE: PRT
<213> ORGANISM: Petunia hybrida

<400> SEQUENCE: 8

Met Gly Arg Lys Glu Ser Asp Asp Gly Val Glu Arg Ile Glu Gly Gly
1               5                   10                  15

Val Val Val Asn Pro Lys Pro Lys Lys Gly Ile Thr Ala Lys Ala
                20                  25                  30

Ile Asp Leu Leu Glu Lys Val Ile Lys Leu Met His Asp Ser Ser
        35                  40                  45

Lys Pro Leu His Tyr Leu Ser Gly Asn Phe Ala Pro Thr Asp Glu Thr
    50                  55                  60

Pro Pro Leu Asn Asp Leu Pro Ile Lys Gly His Leu Pro Glu Cys Leu
65                  70                  75                  80

Asn Gly Glu Phe Val Arg Val Gly Pro Asn Pro Lys Phe Ala Pro Val
                85                  90                  95

Ala Gly Tyr His Trp Phe Asp Gly Asp Gly Met Ile His Gly Leu Arg
                100                 105                 110

Ile Lys Asp Gly Lys Ala Thr Tyr Val Ser Arg Tyr Val Arg Thr Ser
            115                 120                 125

Arg Leu Lys Gln Glu Glu Phe Phe Glu Gly Ala Lys Phe Met Lys Ile
    130                 135                 140

Gly Asp Leu Lys Gly Leu Phe Gly Leu Phe Thr Val Tyr Met Gln Met
145                 150                 155                 160

Leu Arg Ala Lys Leu Lys Ile Leu Asp Thr Ser Tyr Gly Asn Gly Thr
                165                 170                 175

Ala Asn Thr Ala Leu Val Tyr His His Gly Lys Leu Leu Ala Leu Ser
                180                 185                 190

Glu Ala Asp Lys Pro Tyr Ala Leu Lys Val Leu Glu Asp Gly Asp Leu
            195                 200                 205

Gln Thr Leu Gly Met Leu Asp Tyr Asp Lys Arg Leu Leu His Ser Phe
    210                 215                 220

Thr Ala His Pro Lys Val Asp Pro Val Thr Gly Glu Met Phe Thr Phe
225                 230                 235                 240

Gly Tyr Ala His Glu Pro Pro Tyr Ile Thr Tyr Arg Val Ile Ser Lys
                245                 250                 255
```

-continued

```
Asp Gly Ile Met Gln Asp Pro Val Pro Ile Thr Ile Pro Glu Ala Ile
            260             265             270

Met Met His Asp Phe Ala Ile Thr Glu Asn Tyr Ala Ile Met Met Asp
        275             280             285

Leu Pro Leu Cys Phe Arg Pro Lys Glu Met Val Lys Asn Asn Gln Leu
        290             295             300

Ala Phe Thr Phe Asp Thr Thr Lys Lys Ala Arg Phe Gly Val Leu Pro
305             310             315             320

Arg Tyr Ala Lys Ser Glu Ala Leu Ile Arg Trp Phe Glu Leu Pro Asn
            325             330             335

Cys Phe Ile Phe His Asn Ala Asn Ala Trp Glu Glu Gly Asp Glu Val
            340             345             350

Val Leu Ile Thr Cys Arg Leu Pro His Pro Asp Leu Asp Met Val Asn
            355             360             365

Gly Glu Val Lys Glu Asn Leu Glu Asn Phe Ser Asn Glu Leu Tyr Glu
            370             375             380

Met Arg Phe Asn Met Lys Ser Gly Ala Ala Ser Gln Lys Lys Leu Ser
385             390             395             400

Glu Ser Ser Val Asp Phe Pro Arg Ile Asn Glu Asn Tyr Thr Gly Arg
            405             410             415

Lys Gln Arg Tyr Val Tyr Gly Thr Thr Leu Asn Ser Ile Ala Lys Val
            420             425             430

Thr Gly Ile Ile Lys Phe Asp Leu His Ala Glu Pro Glu Thr Gly Lys
            435             440             445

Lys Gln Leu Glu Val Gly Gly Asn Val Gln Gly Ile Phe Asp Leu Gly
450             455             460

Pro Gly Arg Phe Gly Ser Glu Ala Val Phe Val Pro Ser Gln Pro Gly
465             470             475             480

Thr Glu Cys Glu Glu Asp Asp Gly Tyr Leu Ile Phe Phe Val His Asp
            485             490             495

Glu Asn Thr Gly Lys Ser Ala Val Asn Val Ile Asp Ala Lys Thr Met
            500             505             510

Ser Ala Glu Pro Val Ala Val Val Glu Leu Pro Lys Arg Val Pro Tyr
            515             520             525

Gly Phe His Ala Phe Phe Val Thr Glu Glu Gln Ile Gln Glu Gln Ala
            530             535             540

Lys Leu
545
```

PRODUCTION OF CAROTENOIDS AND APOCAROTENOIDS

CROSS-REFERENCE TO RELATED APPLICATIONS

This application claims the benefit of priority of Singapore application No. 10201701500U, filed 24 Feb. 2017, the contents of it being hereby incorporated by reference in its entirety for all purposes.

This application includes a sequence listing submitted electronically by the file name 56126US ST25; Size: 19,666 bytes; Created: Sep. 9, 2023, and is incorporated herein by reference.

FIELD OF THE INVENTION

The invention is in the field of carotenoids and apocarotenoids, in particular, the invention relates to improved methods for producing apocarotenoids and carotenoids.

BACKGROUND OF THE INVENTION

Carotenoids are one group of natural products synthesized in many plants, algae and certain bacteria and fungi. Carotenoids have many unsaturated carbon bounds and these bounds are conjugated, which contribute to distinct features, the bright colors (ranging from pale yellow to orange to red) and potent anti-UV and antioxidant effects. Because of these features, carotenoids have been widely used as natural colorings and nutraceuticals. Particularly, phytoene has effective UVB-absorbing capability and reduces the melanin synthesis in human skin, thus with a growing market in cosmetics. Lycopene, β-carotene and α-carotene are well-known for their antioxidant effects and have been widely used in food, cosmetics, nutraceutical and animal feeds products.

Apocarotenoids are a class of compounds derived from carotenoids by carotenoid cleavage oxygenases. Widely distributed in bacteria, fungi, plants and animals, apocarotenoids act as aroma and scent compounds (α- and β-ionone), photosensory pigment (bixin, crocin), hormones (abscisic acid) and signalling compounds (strigolactones). Among various apocarotenoids, α- and β-ionone are two important aromatic compounds. α-ionone has a sweet and violet-like aroma with odour threshold of ~0.4 ppb. Its isomer, β-ionone, has a warm, woody, and violet aroma and an even lower odour threshold of ~0.007 ppb in air and 1 ppb in water. Due to their significantly low odour threshold and pleasant smell, they are widely exploited in cosmetics and perfume industry. Besides ionones, retinol (or vitamin A) is another commercially important apocarotenoid. Retinol plays an essential function in vision, bone development and skin health as antioxidants. As active cosmetic ingredients and effective medicines for skin diseases, the retinol market size is estimated to be about 1.6 billion dollars.

Despite their high commercial values, supply of natural ionones and retinoids is severely limited by their extremely low abundance in nature. Ionones are present in sub-ppm level in many flowers and fruits, such as rose, sweet *osmanthus*, orris root and raspberry. For instance, it requires 100 tons of raspberries, or 20 hectares of agricultural area, to produce merely 1 gram of α-ionone. As for retinoids, there is no natural source from plants. Exceptionally low amount of retinoids exists in some animal-derived food, such as eggs and butter. Hence, the current supply through extraction from natural sources cannot meet the increasing demands for natural ionones and retinoids. Although these compounds could be chemically synthesized, apocarotenoids such as α-ionone have chiral centres, and synthetic ones are usually a mixture of different enantiomers. The different isomers of many fragrance compounds are known to have different odors, thus it is important to synthesize single isomer instead of a mixture of isomers. More importantly, consumers tend to prefer natural to synthetic flavours and thus natural ingredients have significantly higher prices. The production of α-ionone was previously demonstrated in engineered *Escherichia coli*, but with a very low yield.

Thus, there is a need to provide naturally produced compounds with improved yields.

SUMMARY

In one aspect, there is provided a method for producing a carotenoid or apocarotenoid comprising the step of expressing in a host cell an expression module comprising an expression vector having a coding region encoding at least one optimised carotenoid or apocarotenoid generating enzyme, the coding region being operably linked to a promoter.

In one aspect, there is provided a host cell comprising an expression vector having a coding region encoding at least one optimised carotenoid or apocarotenoid generating enzyme, the coding region being operably linked to a promoter.

In one aspect, there is provided a kit when used in the method as described herein, for the production of a carotenoid comprising one or more of: a first vector encoding one or more optimised first gene products selected from atoB, hmgS, thmgR; a second vector encoding one or more optimised second gene products selected from mevK, pmk, pmd or idi operably linked to a promoter; a third vector encoding one or more optimised third gene products selected from ispA, crtE or crtB, optionally crtI, operably linked to a promoter for the production of phytoene or lycopene.

In one aspect, there is provided a system for producing a carotenoid or apocarotenoid comprising an expression vector having a coding region encoding at least one optimised carotenoid or apocarotenoids generating enzyme, the coding region being operably linked to a promoter, wherein said at least one optimised carotenoid or apocarotenoids generating enzyme is selected from: a. ΔN50-LsLcyE and TrxA-CCD1 (preferably TrxA-*Osmanthus fragans* CCD1) for the production of α-ionone; or b. crtY and CCD1 (preferably *Petunia* hybrid CCD1) for the production of β-ionone; or c. ΔN50-LsLcyE for the production of ε-carotene; or d. crtY and blh for the production of retinal or retinol.

In one aspect, there is provided a kit when used in the method as described herein, for the production of a carotenoid or apocarotenoid comprising one or more of: a first vector encoding one or more optimised first gene products selected from atoB, hmgS, thmgR and optionally crtY operably linked to a promoter; a second vector encoding one or more optimised second gene products selected from mevK, pmk, pmd or idi operably linked to a promoter; a third vector encoding one or more optimised third gene products selected from ispA, crtE, crtB or crtI operably linked to a promoter; and a fourth vector encoding one or more optimised gene products selected from: a. ΔN50-LsLcyE and TrxA-*Osmanthus fragrans* CCD1 operably linked to a promoter for the production of α-ionone; or b. crtY and phCCD1 operably linked to a promoter for the production of β-ionone; or c. ΔN50-LsLcyE operably linked to a promoter for the production of ε-carotene;

or d. crtY and blh operably linked to a promoter for the production of retinal or retinol.

In one aspect, a method for producing a carotenoid or apocarotenoid comprising the steps of: a. contacting a host cell as described herein in a chemically defined media with a substrate for apocarotenoid or carotenoid production; b. incubating the host cell in said chemically defined media to produce one or more preselected carotenoid or apocarotenoid, and c. extracting the one or more preselected carotenoid or apocarotenoids from the chemically defined media using an organic layer.

Definitions

As used herein the term "coding region", also known as the coding sequence or CDS (from coding DNA sequence), is that portion of DNA or RNA, composed of exons, that codes for protein.

As used herein an "operon" refers to group of genes or a segment of DNA that functions as a single transcription unit. It may be comprised of an operator, a promoter, and one or more structural genes that are transcribed into one polycistronic mRNA.

BRIEF DESCRIPTION OF THE DRAWINGS

The invention will be better understood with reference to the detailed description when considered in conjunction with the non-limiting examples and the accompanying drawings, in which:

FIG. 6 shows the production of ε-carotene in the lycopene accumulating $E.\ coli$ strain. Carotenoid production of strains expressing different forms of LCYe enzymes. An illustration of promoters and regulated genes for different strains. Different N-terminal truncated LCYe from $Lactuca\ sativa$ was tested. The abbreviations are as follows. LL, wild-type LCYe enzyme from $Lactuca\ sativa$; L25, LCYe enzyme with the first 25 amino acids removed; L34, LCYe enzyme with the first 34 amino acids removed; L50, LCYe enzyme with the first 50 amino acids removed; L75, LCYe enzyme with the first 75 amino acids removed; L92, LCYe enzyme with the first 92 amino acids removed; L100, LCYe enzyme with the first 100 amino acids removed. See strain description in Table 3. All the measurements were average of triplicates with standard error bar shown in the figure. The percentage of & carotene in the final total carotenoids (lycopene+δ-carotene+ε-carotene) were also indicated.

FIG. 15 demonstrates the metabolic engineering strategies employed for the production of β-ionone. Comparison of wild-type OfCCD1, N-terminal modified OfCCD1 and supplementation of crtY. In Of, TOf and crtY strain, the operon/gene crtY-OfCCD1, crtY-TrxA-OfCCD1 and crtY were expressed, respectively. In TOf+Y strain, additional copy of crtY gene was supplemented in the p15A-spec vector. (A) Ionone production in engineered strain. Strain crtY was the control strain that did not express CCD1 gene thus only produced β-carotene. (B) Accumulated carotenoids in the engineered strain. (C) Biomass of the engineered strains. Although thioredoxin fusion failed to improve β-ionone production, it resulted in a 37-fold increase in the production of the by-product psi-ionone which was converted from lycopene by TOfCCD1. The supplementation of additional crtY effectively converted more lycopene towards β-carotene, thus β-ionone production was significantly improved and psi-ionone was significantly reduced.

FIG. 18 shows the alignment of different CCD1 variants (SEQ ID NOs: 5-8) in this study. Alignment was done by Clustal Omega multiple sequence alignment tool. The information about CCD1 was summarized in Table 4.

FIG. 21 shows the screening of CCD2 and CCD4 with better activity and selectivity. The top graph shows the use of β-carotene as substrate for β-ionone production. The bottom graph shows the use of carotene as substrate for α-ionone production.

DETAILED DESCRIPTION OF THE PRESENT INVENTION

Figure 1:
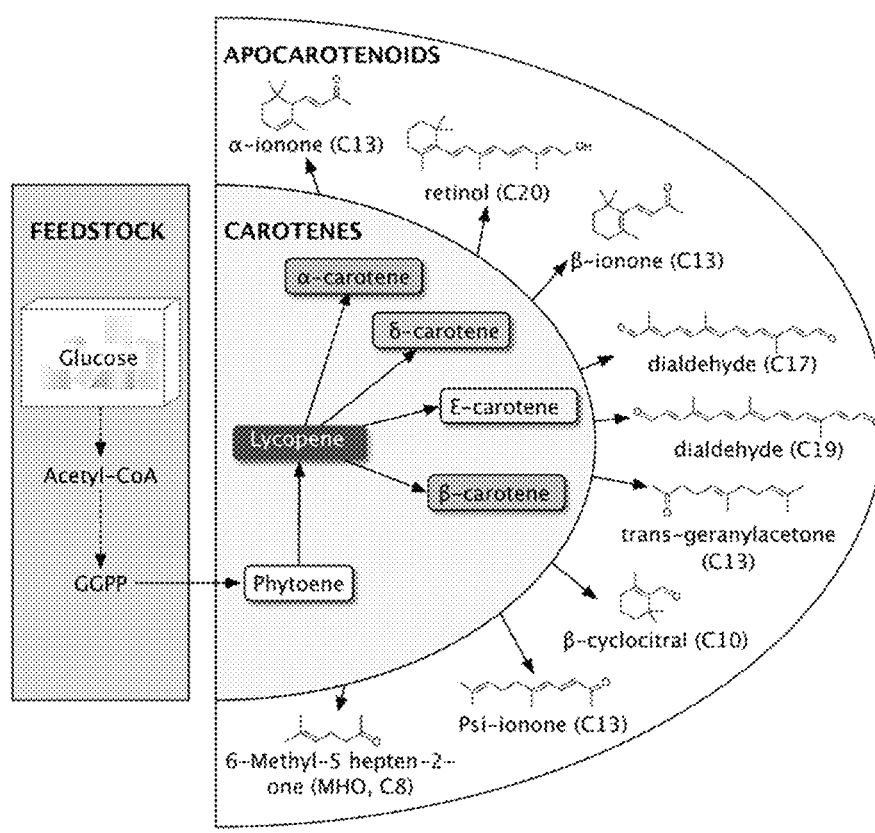
FIG. 1 is a diagram of the 'plug-n-play' platform for the biosynthesis of carotenes and apocarotenoids. Feedstock is inexpensive sugars (such as glucose) or glycerol. The platform could produce various carotenes (phytoene, lycopene, α-carotene, β-carotene, δ-carotene and ε-carotene) and apocarotenoids (α-ionone, β-ionone, psi-ionone, retinol, dialdehydes (C17 and C19), geranylacetone, β-cyclocitral and 6-methyl-5-hepten-2-one (MHO)).

In a first aspect the present invention refers to a method for producing a carotenoid or apocarotenoid. The method comprises the step of expressing in a host cell an expression module comprising an expression vector having a coding region encoding at least one optimised carotenoid or apocarotenoid generating enzyme, the coding region being operably linked to a promoter.

The carotenoid may be selected from phytoene, lycopene, α-carotene, γ-carotene, δ-carotene, ε-carotene or β-carotene and wherein the apocarotenoid may be selected from α-ionone, β-ionone, pseudo-ionone (or psi-ionone), hydroxyionone, β-cyclocitral, trans-geranylacetone, 6-methyl-5-hepten-2-one (MHO), retinal, retinol, 8',10-diapocarotene-8',10-dial (C17) or 10',6-diapocarotene-10',6-dial (C19).

The lycopene cyclase may be selected from lycE or crtY or their truncated forms.

The at least one optimised apocarotenoid generating enzyme, as described herein, may be selected from crtY, CCD1, CCD2, CCD4, BCDO, LcyE, blh or ybbO.

The CCD2 may be selected from CaCCD2 or CsCCD2. The CCD4 may be selected from the group consisting of AtCCD4, BoCCD4b, CmCCD4, CsCCD4a, MaCCD4, MdCCD4, OfCCD4, PpCCD4, RdCCD4 and VvCCD4a.

In one embodiment, the apocarotenoid may be α-ionone and the at least one optimised apocarotenoid generating enzyme may be selected from LcyE and CCD1, and may form an operon having the structure: LcyE-CCD1.

In some embodiments, the LcyE may be derived from *Lactuca sativa* and is N-terminal truncated (ranging from 1 to 100 amino acids of LsLcyE, especially ΔN50-LsLcyE).

The CCD1 may be expressed as a fusion protein selected from TrxA-CCD1, SUMO-CCD1 or MBP-CCD1.

In some embodiments, the fusion protein is TrxA-CCD1. The fusion protein may be selected from TrxA-*Osmanthus fragrans* CCD1 or TrxA-*Petunia* hybrid CCD1.

In some embodiments, the CCD1 may be derived from or *Osmanthus fragrans* (OfCCD1). In some embodiments, the OfCCD1, as described herein, may be optimized between amino acid positions F148 to I167. In particular, the OfCCD1 may comprise one or more of the following mutations: N154Y, M152T, L151F.

In some embodiments, the method may comprise screening for an expression level of α-ionone in an amount of from 10 to 1000 mg/L; from 200 to 800 mg/L; from 300 to 700 mg/L; from 400 to 600 mg/L in a 24 hour period. In some embodiments, the amount of α-ionone is about 500 mg/L in a 24 hour period.

In some embodiments, the apocarotenoid is β-ionone. The at least one optimised apocarotenoid generating enzyme may be selected from crtY and CCD1, and may form an operon having the structure crtY-CCD1. In some embodiments, the crtY as described herein may be derived from *Pantoea ananatis*.

In some embodiments, the CCD1 as described herein may be derived from *Petunia hybrida* (PhCCD1).

In some embodiments, the method may further comprise screening for an expression level of β-ionone in an amount of from 10 to 1000 mg/L; from 200 to 800 mg/L; from 300 to 700 mg/L; from 400 to 600 mg/L in a 24 hour period. In some embodiments, the amount of α-ionone is about 500 mg/L in a 24 hour period.

The apocarotenoid may be retinal or retinol. In one embodiment, the apocarotenoid may be retinal. The at least one optimised apocarotenoid generating enzyme may be selected from crtY and blh, and may form an operon having the structure crtY-blh. In some embodiments, the apocarotenoid may be retinol. The at least one optimised apocarotenoid generating enzyme may be selected from crtY, blh or ybbO, and may form an operon having the structure crtY-blh-ybbO. In some embodiments, the crtY as described herein may be derived from *Pantoea ananatis*. In some embodiments, the blh as described herein may be derived from Uncultured marine bacterium HF10_19P19. In some embodiments, the method may further comprise screening for an expression level of retinal in an amount of from 10 to 1000 mg/L; from 200 to 800 mg/L; from 300 to 700 mg/L; from 400 to 600 mg/L in a 24 hour period. In some embodiments, the amount of α-ionone is about 500 mg/L in a 24 hour period.

The carotenoid may be ε-carotene. The at least one optimised carotenoid generating enzyme may be LcyE. In some embodiments, the LcyE may be derived from *Lactuca sativa* (LsLcyE) and may be N-terminal truncated. In some embodiments, the LsLcyE may comprise an N-terminal truncation of from 1-100 amino acids; from 30-70 amino acids or from 40-60 amino acids. In some embodiments, the LsLcyE comprises an N-terminal truncation of 50 amino acids (ΔN50-LsLcyE).

In some embodiments, the method may further comprise expressing in said host cell: a first expression module comprising an expression vector having a first coding region encoding one or more optimised first gene products selected from atoB, hmgS, thmgR and optionally crtY, the first coding region being operably linked to a promoter; a second expression module comprising an expression vector having second coding region encoding one or more optimised second gene products selected from mevK, pmk, pmd or idi, the second coding region being operably linked to a promoter; a third expression module comprising an expression vector having a third coding region encoding one or more optimised third gene products selected from ispA, crtE, crtB or crtI, the third coding region being operably linked to a promoter.

In some embodiments, the one or more first gene products may form an operon having the structure: atoB-hmgS-thmgR.

In some embodiments, the one or more first gene products may form an operon having the structure: crtY-atoB-hmgS-thmgR.

In some embodiments, the one or more second gene products may form an operon having the structure: mevK-pmk-pmd-idi.

In some embodiments, the one or more third gene products may form an operon having the structure: crtE-crtB-ispA.

In some embodiments, the one or more third gene products may form an operon having the structure: crtE-crtB-crtI-ispA.

The host cell as described herein may be *Escherichia coli* selected from BL21 DE3 or MG1655 DE3.

The promoter may be selected from one or more of TM1, TM2 or TM3, T7 RNA polymerase promoter, a T5 RNA polymerase promoter, a T3 RNA polymerase promoter, an SP6 RNA polymerase promoter or an inducible promoter.

In some embodiments, the optimisation of the apocarotenoid generating enzyme and optimised gene products is achieved by codon optimization or site-directed mutagenesis.

In another aspect, there is provided a host cell comprising an expression module comprising expression vector having a coding region encoding at least one optimised apocarotenoid or carotenoid generating enzyme, the coding region being operably linked to a promoter.

In some embodiments, the at least one optimised apocarotenoid generating enzyme may be selected from crtY, CCD1, CCD2, CCD4, BCDO, LcyE, blh or ybbO.

The host cell may further comprise a first expression module comprising an expression vector having a first coding region encoding one or more optimised first gene products selected from atoB, hmgS, thmgR and optionally crtY, the first coding region being operably linked to a promoter; a second expression module comprising an expression vector having a second coding region encoding one or more optimised second gene products selected from mevK, pmk, pmd or idi, the second coding region being operably linked to a promoter; a third expression module comprising an expression vector having a third coding region encoding one or more optimised third gene products selected from ispA, crtE, crtB or crtI, the third coding region being operably linked to a promoter.

In another aspect, there is provided a vector encoding one or more optimised gene products selected from atoB, hmgS, thmgR and optionally crtY operably linked to a promoter.

In another aspect, there is provided a vector encoding one or more optimised gene products selected from mevK, pmk, pmd or idi operably linked to a promoter.

In another aspect, there is provided a vector encoding one or more optimised gene products selected from ispA, crtE, crtB or crtI operably linked to a promoter.

In another aspect, there is provided a vector encoding one or more optimised gene products selected from crtY, CCD1, BCDO, LcyE, blh or ybbO operably linked to a promoter.

In some embodiments, the optimised gene products may be selected from the group consisting of ΔN50-LsLcyE and TrxA-*Osmanthus fragrans* CCD1; crtY and phCCD1; ΔN50-LsLcyE; crtY and blh, and crtY, blh and ybbO.

In another aspect, there is provided a system for producing an carotenoid or apocarotenoid comprising an expression module comprising an expression vector having a coding region encoding at least one optimised carotenoid or apocarotenoid generating enzyme, the coding region being operably linked to a promoter, wherein said at least one optimised carotenoid or apocarotenoid generating enzyme is selected from: a. ΔN50-LsLcyE and TrxA-*Osmanthus fragrans* CCD1 for the production of α-ionone; or b. crtY and phCCD1 for the production of β-ionone; or c. ΔN50-LsLcyE for the production of ε-carotene; or d. crtY and blh for the production of retinal or retinol; or e. crtY, blh and ybbO for the production of retinol.

In some embodiments, the system may further comprise: a first expression module comprising an expression vector having a first coding region encoding one or more optimised first gene products selected from atoB, hmgS, thmgR and optionally crtY, the first coding region being operably linked to a promoter; a second expression module comprising an expression vector having second coding region encoding one or more optimised second gene products selected from mevK, pmk, pmd or idi, the second coding region being operably linked to a promoter; a third expression module comprising an expression vector having a third coding region encoding one or more optimised third gene products selected from ispA, crtE, crtB or crtI, the third coding region being operably linked to a promoter.

In another aspect, there is provided a kit when used in the method as described herein, for the production of a carotenoid or apocarotenoid comprising one or more of: a first vector encoding one or more optimised first gene products selected from atoB, hmgS, thmgR; a second vector encoding one or more optimised second gene products selected from mevK, pmk, pmd or idi operably linked to a promoter; a third vector encoding one or more optimised third gene products selected from ispA, crtE or crtB, optionally crtI, operably linked to a promoter for the production of phytoene or lycopene.

In another aspect, there is provided a kit when used in the method as described herein, for the production of an apocarotenoid or carotenoid comprising one or more of: a first vector encoding one or more optimised first gene products selected from atoB, hmgS, thmgR and optionally crtY operably linked to a promoter; a second vector encoding one or more optimised second gene products selected from mevK, pmk, pmd or idi operably linked to a promoter; a third vector encoding one or more optimised third gene products selected from ispA, crtE, crtB or crtI operably linked to a promoter; and a fourth vector encoding one or more optimised gene products selected from: a. ΔN50-LsLcyE and TrxA-*Osmanthus fragrans* CCD1 operably linked to a promoter for the production of α-ionone; or b. crtY and phCCD1 operably linked to a promoter for the production of β-ionone; or c. ΔN50-LsLcyE operably linked to a promoter for the production of ε-carotene; or d. crtY and blh operably linked to a promoter for the production of retinal; or e. crtY, blh and ybbO for the production of retinol.

In another aspect, there is provided a method for producing an apocarotenoid or carotenoid comprising the steps of: a. contacting a host cell as described herein in a chemically defined media with a substrate for apocarotenoid or carotenoid production; b. incubating the host cell in said chemically defined media to produce one or more preselected apocarotenoids or carotenoids, and c. extracting the one or more preselected apocarotenoids or carotenoids from the chemically defined media using an organic layer.

In some embodiments, the organic layer may be coconut oil or soybean oil or other edible oils.

In some embodiments, the apocarotenoid may be selected from α-ionone, β-ionone, pseudo-ionone (or psi-ionone), hydroxy-ionone, trans-geranylacetone, 6-methyl-5-hepten-2-one (MHO), retinal, retinol, 8',10-diapocarotene-8',10-dial (C17) or 10',6-diapocarotene-10',6-dial (C19) and wherein the carotenoid may be selected from phytoene, lycopene, α-carotene, γ-carotene, δ-carotene, ε-carotene or β-carotene.

The invention illustratively described herein may suitably be practiced in the absence of any element or elements, limitation or limitations, not specifically disclosed herein. Thus, for example, the terms "comprising", "including", "containing", etc. shall be read expansively and without limitation. Additionally, the terms and expressions employed herein have been used as terms of description and not of limitation, and there is no intention in the use of such terms and expressions of excluding any equivalents of the features shown and described or portions thereof, but it is recognized that various modifications are possible within the scope of the invention claimed. Thus, it should be understood that although the present invention has been specifically disclosed by preferred embodiments and optional features, modification and variation of the inventions embodied therein herein disclosed may be resorted to by those skilled in the art, and that such modifications and variations are considered to be within the scope of this invention.

The invention has been described broadly and generically herein. Each of the narrower species and subgeneric groupings falling within the generic disclosure also form part of the invention. This includes the generic description of the invention with a proviso or negative limitation removing any subject matter from the genus, regardless of whether or not the excised material is specifically recited herein.

Other embodiments are within the following claims and non-limiting examples. In addition, where features or aspects of the invention are described in terms of Markush groups, those skilled in the art will recognize that the invention is also thereby described in terms of any individual member or subgroup of members of the Markush group.

Experimental Section

Non-limiting examples of the invention and comparative examples will be further described in greater detail by reference to specific Examples, which should not be construed as in any way limiting the scope of the invention.

Materials and Methods

*E. coli* Bl21-Gold DE3 strain (Stratagene) was used in this study. The genes hmgS, hmgR, mevK, pmk and pmd (or MVD1) were amplified by PCR using the chromosomal DNA of *Saccharomyces cerevisiae*. The genes atoB and idi were amplified from *E. coli* genomic DNA. All the genes were cloned into two plasmids, p15A-spec-hmgS-atoB-hmgR (L2-8) and p15A-cam-mevK-pmk-pmd-idi (L2-5). The genes in the lycopene biosynthetic pathway (crtEBI) amplified from the pAC-LYC plasmid was introduced into p15A-kan-crtEBI-ispA plasmid. The LCYe gene from *Lactuca sativa* (LsLCYe enzyme), the crtY gene from *Pantoea ananatis*, the CCD1 gene from *Arabidopsis thaliana, Osmanthus fragrans, Vitis vinifera* and *Petunia* hybrid and the blh genes from Uncultured marine bacterium HF10_19P19 (blh1) and Uncultured marine bacterium 66A03 (blh2) were codon optimized and synthesized by Integrated DNA Technologies. The LsLCYe gene and crtY gene was first cloned into the plasmid p15A-amp-LsLCYe (L2-9), and p15A-amp-crtY (L2-9), respectively. OfCCD1 gene was inserted into p15A-amp-LsLCYe (L2-9) plasmid. Different CCD1 or blh genes were later inserted into p15A-amp-crtY (L2-9) strain. Site-directed mutagenesis was introduced from primers synthesized by Integrated DNA Technologies. Additional copy of crtY was inserted into p15A-spec-hmgS-atoB-hmgR (L2-8) plasmid. All the p15A plasmids were derived from pAC-LYC plasmid. The stem-loop structure of RNA I in the p15A plasmid origin was mutated to make the plasmids compatible to each other. The T7 promoter variants are TM1, TM2 and TM3 was summarized in Table 1. The information about plasmids and strains was summarized in Table 2 and 3.

Table 1 summarizes the promoter sequences used.

| Promoter Name | Sequence |
|---|---|
| T7 | TAATACGACTCACTATAGGGGAATTGTGAGCG |
| TM1 | TAATACGACTCACTAATGGGGAATTGTGAGCG |
| TM2 | TAATACGACTCACTCGAGGGGAATTGTGAGCG |
| TM3 | TAATACGACTCACTATAAAGGAATTGTGAGCG |

Table 2 summarizes the strains and plasmids used.

| Strains or plasmids | Descriptions |
|---|---|
| BL21 DE3 | *E. coli* Bl21-Gold DE3 strain (Stratagene). |
| p15A-spec-hmgS-atoB-hmgR (L2-8) | P15A vector carrying atoB-hmgS-hmgR operon controlled by TM1 promoter, with p15A origin mutated |
| p15A-crtY-spec-hmgS-atoB-hmgR (L2-8) | P15A vector carrying crtY-atoB-hmgS-hmgR operon controlled by TM1 promoter, with p15A origin mutated |
| p15A-cam-mevK-pmk-pmd-idi (L2-5) | P15A vector carrying mevK-pmk-pmd-idi operon controlled by TM2 promoter, with p15A origin mutated |
| p15A-kan-crtEBI-ispA | P15A vector carrying crtEBI-ispA operon controlled by TM1 promoter |
| p15A-amp-LsLCYe (L2-9) | P15A vector carrying LsLCYe gene controlled by TM1 promoter, with p15A origin mutated |
| p15A-amp-ΔN25LsLCYe (L2-9) | P15A vector carrying LsLCYe gene, with the first 25 amino acid removed, controlled by TM1 promoter, with p15A origin mutated |
| p15A-amp-ΔN34LsLCYe (L2-9) | P15A vector carrying LsLCYe gene, with the first 34 amino acid removed, controlled by TM1 promoter, with p15A origin mutated |
| p15A-amp-ΔN50LsLCYe (L2-9) | P15A vector carrying LsLCYe gene, with the first 50 amino acid removed, controlled by TM1 promoter, with p15A origin mutated |
| p15A-amp-ΔN75LsLCYe (L2-9) | P15A vector carrying LsLCYe gene, with the first 75 amino acid removed, controlled by TM1 promoter, with p15A origin mutated |
| p15A-amp-ΔN92LsLCYe (L2-9) | P15A vector carrying LsLCYe gene, with the first 92 amino acid removed, controlled by TM1 promoter, with p15A origin mutated |
| p15A-amp-ΔN100LsLCYe (L2-9) | P15A vector carrying LsLCYe gene, with the first 100 amino acid removed, controlled by TM1 promoter, with p15A origin mutated |
| p15A- amp-LsLCYe-OfCCD1 (L2-9) | p15A-amp-LsLCYe (L2-9) containing OfCCD1 gene |
| p15A-amp-ΔN50LsLCYe-OfCCD1 (L2-9) | p15A-amp-ΔN50LsLCYe (L2-9) containing OfCCD1 gene |
| p15A-amp-ΔN50LsLCYe-SUMO-OfCCD1 (L2-9) | p15A-amp-ΔN50LsLCYe (L2-9) containing OfCCD1 gene with SUMO fusion |
| p15A-amp-ΔN50LsLCYe-MBP-OfCCD1 (L2-9) | p15A-amp-ΔN50LsLCYe (L2-9) containing OfCCD1 gene with MBP fusion |
| p15A-amp-ΔN50LsLCYe-TrxA-OfCCD1 (L2-9) | p15A-amp-ΔN50LsLCYe (L2-9) containing OfCCD1 gene with trxA fusion |

-continued

| Strains or plasmids | Descriptions |
|---|---|
| p15A-amp-ΔN50LsLCYe-TrxA-OfCCD1_I151F_M152T_N154Y (L2-9) | p15A-amp-ΔN50LsLCYe (L2-9) containing OfCCD1 gene with trxA fusion, and three mutations, namely I151F, M152T, N154Y |
| p15A-amp-crtY (L2-9) | P15A vector carrying crtY gene controlled by TM1 promoter, with p15A origin mutated |
| p15A-amp-crtY-AtCCD1 (L2-9) | p15A-amp-TM1-crtY (L2-9) containing AtCCD1 gene |
| p15A-amp-crtY-OfCCD1 (L2-9) | p15A-amp-TM1-crtY (L2-9) containing OfCCD1 gene |
| p15A-amp-crtY-TrxA-OfCCD1 (L2-9) | p15A-amp-TM1-crtY (L2-9) containing OfCCD1 gene with the trxA fusion |
| p15A-amp-crtY-PhCCD1 (L2-9) | p15A-amp-TM1-crtY (L2-9) containing PhCCD1 gene |
| p15A-amp-crtY-TrxA-PhCCD1 (L2-9) | p15A-amp-TM1-crtY (L2-9) containing PhCCD1 gene with the trxA fusion |
| p15A-amp-crtY-blh1 (L2-9) | p15A-amp-TM1-crtY (L2-9) containing blh gene from Uncultured marine bacterium HF10_19P19 |
| p15A-amp-crtY-blh2 (L2-9) | p15A-amp-TM1-crtY (L2-9) containing blh gene from Uncultured marine bacterium 66A03 |
| pET11a-trxA-CaCCD2 | pET11a vector containing trxA-fused CaCCD2 gene from *Crocus angustifolius* |
| pET11a-trxA-CsCCD2 | pET11a vector containing trxA-fused CsCCD2 gene from *Crocus sativus* |
| pET11a-trxA-AtCCD4 | pET11a vector containing trxA-fused AtCCD4 gene from *Arabidopsis thaliana* |
| pET11a-trxA-BoCCD4b | pET11a vector containing trxA-fused BoCCD4b gene from *Bixa orellana* |
| pET11a-trxA-CmCCD4 | pET11a vector containing trxA-fused CmCCD4 gene from *Chrysanthemum morifolium* |
| pET11a-trxA-CsCCD4a | pET11a vector containing trxA-fused CsCCD4a gene from *Crocus sativus* |
| pET11a-trxA-MaCCD4 | pET11a vector containing trxA-fused MaCCD4 gene from *Musa acuminata* AAA Group |
| pET11a-trxA-MdCCD4 | pET11a vector containing trxA-fused MdCCD4 gene from *Malus domestica* |
| pET11a-trxA-OfCCD4 | pET11a vector containing trxA-fused OfCCD4 gene from *Osmanthus fragran* |
| pET11a-trxA-PpCCD4 | pET11a vector containing trxA-fused PpCCD4 gene from *Prunus persica* |
| pET11a-trxA-RdCCD4 | pET11a vector containing trxA-fused RdCCD4 gene from *Rosa damascena* |
| pET11a-trxA-VvCCD4a | pET11a vector containing trxA-fused VvCCD4a gene from *Vitis vinifera* |

Table 3 describes the strains used in the study.

| No. | Strains name | Descriptions |
|---|---|---|
| 1 | 121 | Strain producing lycopene, with three plasmids p15A-spec-hmgS-atoB-hmgR (L2-8), p15A-cam-mevK-pmk-pmd-idi (L2-5) and p15A-kan-crtEBI-ispA. |
| 2 | 121Y | Strain producing β-carotene, with three plasmids p15A-crtY-spec-hmgS-atoB-hmgR (L2-8), p15A-cam-mevK-pmk-pmd-idi (L2-5) and p15A-kan-crtEBI-ispA. |
| 3 | 121 + LL | Strain producing ε-carotene, Strain 121 with p15A-amp-LsLCYe (L2-9), expressing wildtype LCYe. |
| 4 | 121 + L50 | Strain producing ε-carotene, Strain 121 with p15A-amp-ΔN50LsLCYe (L2-9), expressing LCYe with first 50 amino acid truncated. |
| 5 | 121 + L100 | Strain producing ε-carotene, Strain 121 with p15A-amp-ΔN100LsLCYe (L2-9), expressing LCYe with first 100 amino acid truncated. |
| 6 | 121-LO | Strain producing α-ionone, Strain 121 with p15A-amp-LsLCYe-OfCCD1 (L2-9), expressing wildtype LCYe and wildtype OfCCD1. |
| 7 | 121-L50-O | Strain producing α-ionone, Strain 121 with p15A-amp-LsLCYe-OfCCD1 (L2-9), expressing LCYe with first 50 amino acid truncated and wildtype OfCCD1. |
| 8 | 121-L50-SUMO-O | Strain producing α-ionone, Strain 121 with p15A-amp-ΔN50LsLCYe-SUMO-OfCCD1 (L2-9), expressing LCYe with first 50 amino acid truncated and SUMO-fused OfCCD1. |
| 9 | 121-L50-MBP-O | Strain producing α-ionone, Strain 121 with p15A-amp-ΔN50LsLCYe-MBP-OfCCD1 (L2-9), expressing LCYe with first 50 amino acid truncated and MBP-fused OfCCD1. |

| No. | Strains name | Descriptions |
|---|---|---|
| 10 | 121-L50-TrxA-O | Strain producing α-ionone, Strain 121 with p15A-amp-ΔN50LsLCYe-TrxA-OfCCD1 (L2-9), expressing LCYe with first 50 amino acid truncated and TrxA-fused OfCCD1. |
| 11 | 121-L50-TrxA-O-L151F_M152T_N154Y | Strain producing α-ionone, Strain 121 with p15A-amp-ΔN50LsLCYe-TrxA-OfCCD1_L151F_M152T_N154Y (L2-9), expressing LCYe with first 50 amino acid truncated and TrxA-fused OfCCD1 with three mutations. |
| 12 | Of | Strain producing β-ionone, Strain 121 with p15A-amp-crtY-OfCCD1 (L2-9), expressing crtY and wildtype OfCCD1. |
| 13 | TOf | Strain producing β-ionone, Strain 121 with p15A-amp-crtY-TrxA-OfCCD1 (L2-9), expressing crtY and TrxA-fused OfCCD1. |
| 14 | TOf + Y | Strain producing β-ionone, Strain 121Y with p15A-amp-crtY-TrxA-OfCCD1 (L2-9), expressing crtY and TrxA-fused OfCCD1. |
| 15 | crtY | Strain producing β-carotene, strain 121 with p15A-amp-crtY (L2-9). |
| 16 | Ph | Strain producing β-ionone, Strain 121 with p15A-amp-crtY-PhCCD1 (L2-9), expressing crtY and PhCCD1. |
| 17 | At | Strain producing β-ionone, Strain 121 with p15A-amp-crtY-AtCCD1 (L2-9), expressing crtY and PhCCD1. |
| 18 | Vv | Strain producing β-ionone, Strain 121 with p15A-amp-crtY-VvCCD1 (L2-9), expressing crtY and PhCCD1. |
| 19 | Ph + Y | Strain producing β-ionone, Strain 121Y with p15A-amp-crtY-PhCCD1 (L2-9), expressing crtY and PhCCD1. |
| 20 | TPh | Strain producing β-ionone, Strain 121 with p15A-amp-crtY-TrxA-PhCCD1 (L2-9), expressing crtY and TrxA-fused PhCCD1. |
| 21 | TPh + Y | Strain producing β-ionone, Strain 121Y with p15A-amp-crtY-TrxA-PhCCD1 (L2-9), expressing crtY and TrxA-fused PhCCD1. |
| 22 | Blh1 | Strain producing retinoids, Strain 121 with p15A-amp-crtY-blh1 (L2-9), expressing crtY and blh1. |
| 23 | Blh2 | Strain producing retinoids, Strain 121 with p15A-amp-crtY-blh1 (L2-9), expressing crtY and blh1. |
| 24 | Blh1 + Y | Strain producing retinoids, Strain 121Y with p15A-amp-crtY-blh2 (L2-9), expressing crtY and blh2. |
| 25 | Blh2 + Y | Strain producing retinoids, Strain 121Y with p15A-amp-crtY-blh2 (L2-9), expressing crtY and blh2. |

Media and Culture Conditions

All the cells were grown in 2XPY media (20 g/L Peptone, 10 g/L Yeast extract and 10 g/L NaCl), supplemented with 10 g/L glycerol, 50 mM 4-(2-hydroxyethyl)-1-piperazineethanesulfonic acid (HEPES). For prolonged incubation (48 h), 5 mg/L Tween80 was also added into the media to prevent cell aggregation. Briefly, 104 fresh cell culture was inoculated into 1 mL fresh media in 14 mL BD Falcon™ tube. Cells were initially grown at 37° C. with the shaking speed of 300 rpm and were induced by a range of IPTG concentrations (as indicated in text) when $OD_{600}$ reached around 0.6. After induction, 2004 of dodecane was supplemented onto the culture to extract ionone or retinoids, and the cells were incubated at 28° C. for another 20 h or 48 h before harvest. The media were supplemented with appropriate antibiotics (100 mg/L ampicillin, 34 mg/L chloramphenicol, 50 mg/L kanamycin and 50 mg/L spectinomycin) to maintain corresponding plasmids.

Quantification of Carotenoids and Retinoids

Intracellular carotenoids were extracted from cellular pellets according to the acetone extraction method. Briefly, 10-50 μL bacterial culture (depending on the content of carotenoids in the cells) was collected and centrifuged. Cell pellets were washed with PBS and were resuspended in 20 μL of water, followed by addition of 180 μL of acetone. The HPLC method employed an Agilent 1260 Infinity LC System equipped with a ZORBAX, Eclipse Plus C18, 4.6 mm×250 mm, 5 μm column and diode array detector (DAD). Isocratic condition (50% methanol, 48% ethyl acetate and 2% water) was maintained at 1.5 mL/min for 5 min. The carotenoids were detected at wavelength of 450 nm. Standard curves were generated using commercial standards including ε-carotene, β-carotene, lycopene, retinol and retinal. The extracellular retinoid samples were prepared by diluting 20-504 of organic layer into 1000 μL hexane and analysed by the same HPLC system. Isocratic condition was used as follows. Mobile phase was 95% methanol and 5% acetonitrile and the flow rate was 1.5 ml/min. Retinoids were detected at wavelength of 340 nm.

Quantification of α,β-Ionone and Psi-Ionone

The α, or β-ionone samples were prepared by diluting 20-504 of organic layer into 10004 hexane. The samples were analysed on an Agilent 7980B gas chromatography equipped with Agilent VF-WAXms column and an Agilent 7200 Accurate-Mass Quadrupole Time-of-Flight (GC/MS). Injection of samples was performed in splitless mode at 240° C. The oven program started at 100° C. for 2 min, then the temperature was raised up at 30° C./min until 240° C. and maintained at 240° C. for another 2 min. The ionone concentrations were calculated by interpolating with a standard curve prepared by commercial standards. Mass spectrometer was operated in EI mode with full scan analysis (m/z 30-300, 1 spetra/s).

Chirality Analysis

The chirality of α-ionone from the samples was analyzed with Agilent 7980B gas chromatography equipped with Agilent Cyclosil-B GC Column and an Agilent 7200 Accurate-Mass Quadrupole Time-of-Flight (GC/MS). The oven program started at 80° C. for 2 min, then the temperature was raised up at 5° C./min until 210° C. and to 250° C. at 20° C./min and finally maintained at 250° C. for another 2 min. The ionone concentrations were calculated by interpolating with a standard curve prepared by commercial standards. Mass spectrometer was operated in EI mode with full scan analysis (m/z 30-300, 2 spetra/s).

Fed-Batch Fermentation

Starting medium was a chemically defined medium modified which contained 15 g/L glucose, 2 g/L $(NH_4)_2SO_4$, 4.2 g/L $KH_2PO_4$ and 11.24 g/L $K_2HPO_4$, 1.7 g/L citric acid, 0.5 g/L $MgSO_4$ and 10 mL/L trace element solution. The trace element solution (100×) contained 0.25 g/L $CoCl_2.6H_2O$, 1.5 g/L $MnSO_4.4H_2O$, 0.15 g/L $CuSO_4.2H_2O$, 0.3 g/L $H_3BO_3$, 0.25 g/L $Na_2MoO_4.2H_2O$, 0.8 g/L $Zn(CH_3COO)_2$, 5 g/L Fe(III) citrate, and 0.84 g/L EDTA, pH 8.0. Feed medium (500 g/L glucose and 5 g/L $MgSO_4$) was pumped into the 250 mL Mini Bioreactor (Applikon Biotechnology) at an initial rate of 0.6 mL/h and approximately exponentially increased to at 1.8 mL/h within 12 h and maintained at 1.5 mL/h for another 24 h. Cells were induced by 0.03 mM IPTG when OD reached about 40. After induction, 30 mL of isopropyl myristate was supplemented into the bioreactor to extract ionones.

EXAMPLES

Production of Carotenes by "Plug-n-Play"

Example 1. Optimization of Phytoene Production

Figure 2:
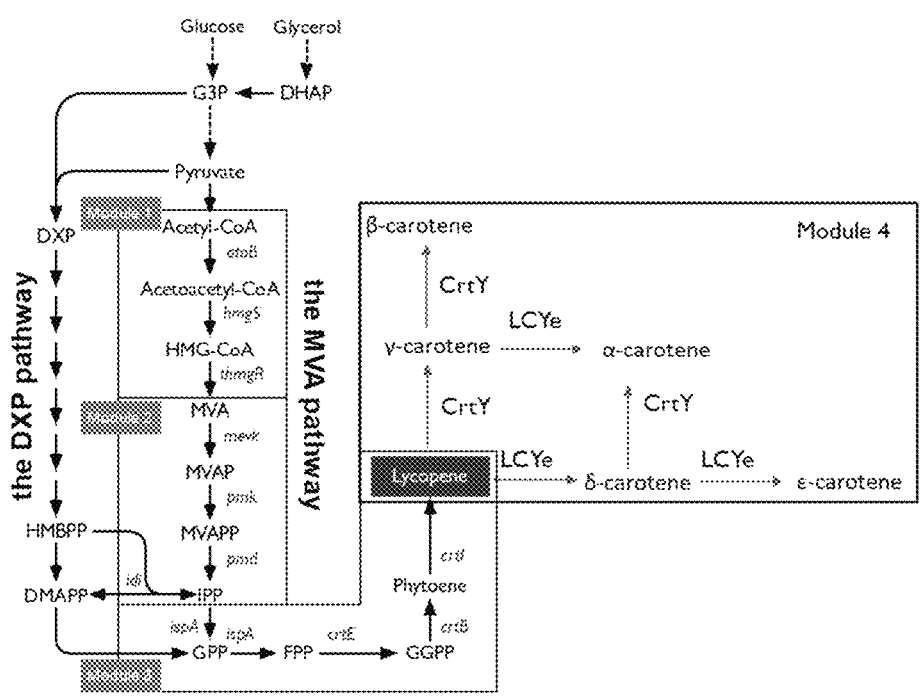
FIG. 2 is a schematic representation of expression modules for carotene synthesis. The upstream MVA pathway (expression module 1), the downstream MVA pathway (module 2), the phytoene or lycopene pathway (expression module 3), the carotene pathway (expression module 4). The genes expressed encode the following enzymes: atoB, Acetoacetyl-CoA thiolase; hmgS, HMG-CoA synthase; thmgR, truncated HMG-CoA reductase; mevk, mevalonate kinase; pmk, phosphomevalonate kinase; pmd, mevalonate pyrophosphate decarboxylase; idi, IPP isomerase; ispA, FPP synthase; crtE, GGPP synthase; crtB, phytoene synthase; crtI, phytoene desaturase; crtY, lycopene-beta-cyclase; LCYe, lycopene-epsilon-cyclase. Abbreviation for the compounds: G3P, D-glyceraldehyde-3-phosphate; DHAP, Dihydroxyacetone phosphate; HMG-CoA, 3-hydroxy-3-methylglutaryl-coenzyme A; MVA, mevalonate; MVAP, phosphomevalonate; MVAPP, diphosphomevalonate; IPP, isopentenyl pyrophosphate; DMAPP, dimethylallyl pyrophosphate; HMBPP, (E)-4-Hydroxy-3-methyl-but-2-enyl pyrophosphate; GPP, geranyl pyrophosphate; FPP, farnesyl pyrophosphate; GGPP, geranylgeranyl pyrophosphate. Dashed arrow indicates multiple enzymatic steps.
Figure 3:
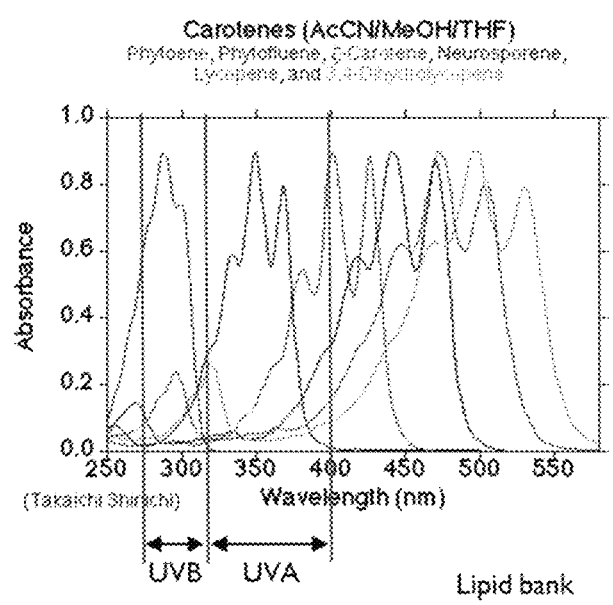
FIG. 3 shows the UV absorbance spectrum of various carotenoids. The UV-B and UV-A wavelength is indicated.
Figure 4:
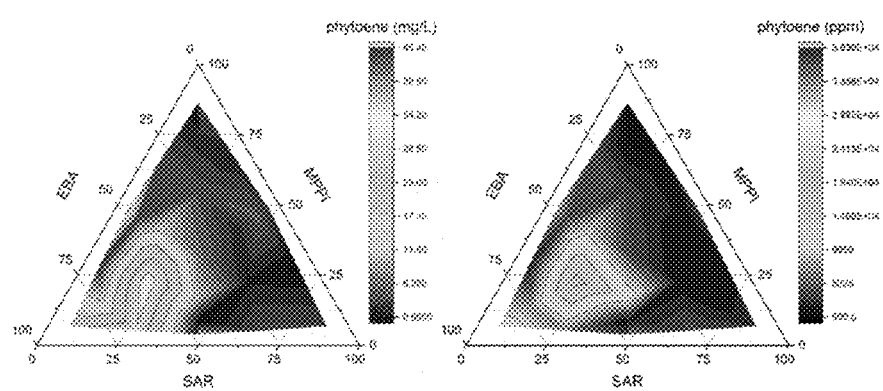
FIG. 4 shows use of an experimental design-aided systematic pathway optimization (EDASPO) method to optimize phytoene production by controlling SAR, MPPI and EBIA modules with T7 promoter variants. The number represents the different strength of T7 promoter variants, with 1, 2 and 3 representing approximately 92%, 37% and 16% of native T7 promoter strength, respectively. Expression module 1, or SAR module, hmgS-atoB-hmgR; Expression module 2, or MPPI module, mevK, pmk, pmd and idi; Expression module 3, or EBA module, phytoene biosynthetic pathway (crtEB and ispA).

The "plug-n-play" as described herein platform produces carotenes and apocarotenoids from inexpensive feedstock (FIG. 1). It is very challenging to maintain high metabolic flux along a recombinant pathway that simultaneously overexpresses 13 enzymes in *E. coli* cells to produce carotenes (FIG. 2). Ultraviolet-B (UVB, 280-310 nm) is the most acute sunlight-induced damage to the skin. The colorless carotene, phytoene, has the maximum UV absorbance at 280 nm (FIG. 3), rendering it an ideal ingredient for topical UV protection agent. Phytoene is the first key intermediate that can be further converted to various C40 carotenoids. To produce phytoene, the biosynthetic pathway from acetyl-CoA was divided into three expression modules (FIG. 2, Module 1, upstream mevalonate pathway including hmgS-atoB-hmgR; Module 2, downstream mevalonate pathway including mevK, pmk, pmd and idi; Module 3, phytoene biosynthetic pathway including crtEB and ispA), and systematically optimized by EDASPO approach. Briefly, the 3 expression modules modules were controlled by three different T7 promoter variants with different strength, and the phytoene yield was then correlated with the promoter strength of each module to locate the optimal transcriptional range for each expression module (Ternary diagram, FIG. 4). As a result, the optimal range for each expression module was identified and an optimized strain (221 strain) was obtained, that produced ~45 mg/L of phytoene in a shake flask, or 38,000 ppm (FIG. 4).

Example 2. Optimization of Lycopene Production

Figure 5:
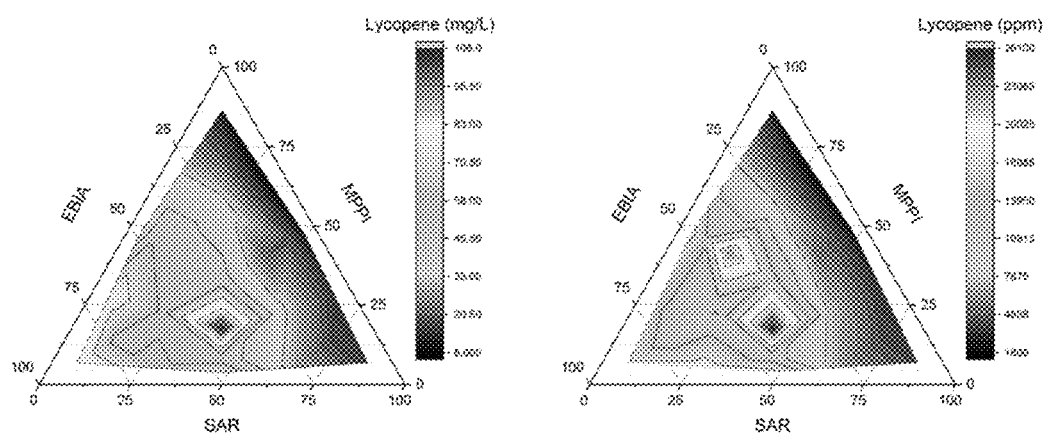
FIG. 5 shows the use of EDASPO method to optimize lycopene production by controlling SAR, MPPI and EBIA expression modules with T7 promoter variants. The number represents the different strength of T7 promoter variants, with 1, 2 and 3 representing approximately 92%, 37% and 16% of native T7 promoter strength, respectively. Expression module 1, or SAR module, hmgS-atoB-hmgR; Expression module 2, or MPPI module, mevK, pmk, pmd and idi; Expression module 3, or EBIA module, lycopene biosynthetic pathway (crtEBI and ispA).

Lycopene is another valuable carotenoid that has potent anti-oxidant effect. The biosynthetic pathway is extremely long and challenging to optimize in heterologous microbial production strain. Here, the pathway was divided into three different modules (FIG. 2, Module 1, upstream mevalonate pathway including hmgS-atoB-hmgR; Module 2, downstream mevalonate pathway including mevK, pmk, pmd and idi; Module 3, lycopene biosynthetic pathway including crtEBI and ispA), and overproduce lycopene by EDASPO approach. Briefly, the 3 expression modules were controlled by three different T7 promoter variants with different strength, and the lycopene yield was then correlated with the promoter strength of each expression module to locate the optimal transcriptional range for each expression module (Ternary diagram, FIG. 5). As a result, the optimal range for each expression module was identified and an optimized strain (121 strain) was obtained, that produced ~107 mg/L of lycopene in a shake flask, or 26,000 ppm (FIG. 5). This lycopene-producing strain served as parental platform strain for further production of downstream carotenoids and apocarotenoids.

Example 3. Optimization of Carotene Production

A fourth biosynthetic expression module can be introduced based on the parental lycopene-overproducing strain (FIG. 2). Depending on the expression levels of crtY and LCYe, α-, β-, δ- γ- and ε-carotene can be produced (FIG. 2). However, ε-carotene is known to be accumulated at very low levels in nature. To date, only the LCYe from *Lactuca sativa* (LsLCYe) is known to preferentially form the bicyclic ε-ring from lycopene. When the wild type LsLCYe enzyme in the lycopene strain (121 strain) was overexpressed, a mixture of δ-carotene (carotene with an ε-ring at one end) and ε-carotene (carotene with two ε-rings at both ends) was produced, with more than 70% lycopene uncyclized (0.1 mM, FIG. 6). The & carotene production was initially optimized by tuning the transcription levels and obtained highest amount of ε-carotene with moderate IPTG induction (0.03 mM). However, the highest ε-carotene titer was merely 18 mg/L (2500 ppm), corresponding to less than 30% in the total carotenoids (FIG. 6), suggesting that the activity of LsLCYe enzyme was insufficient.

Figure 7:
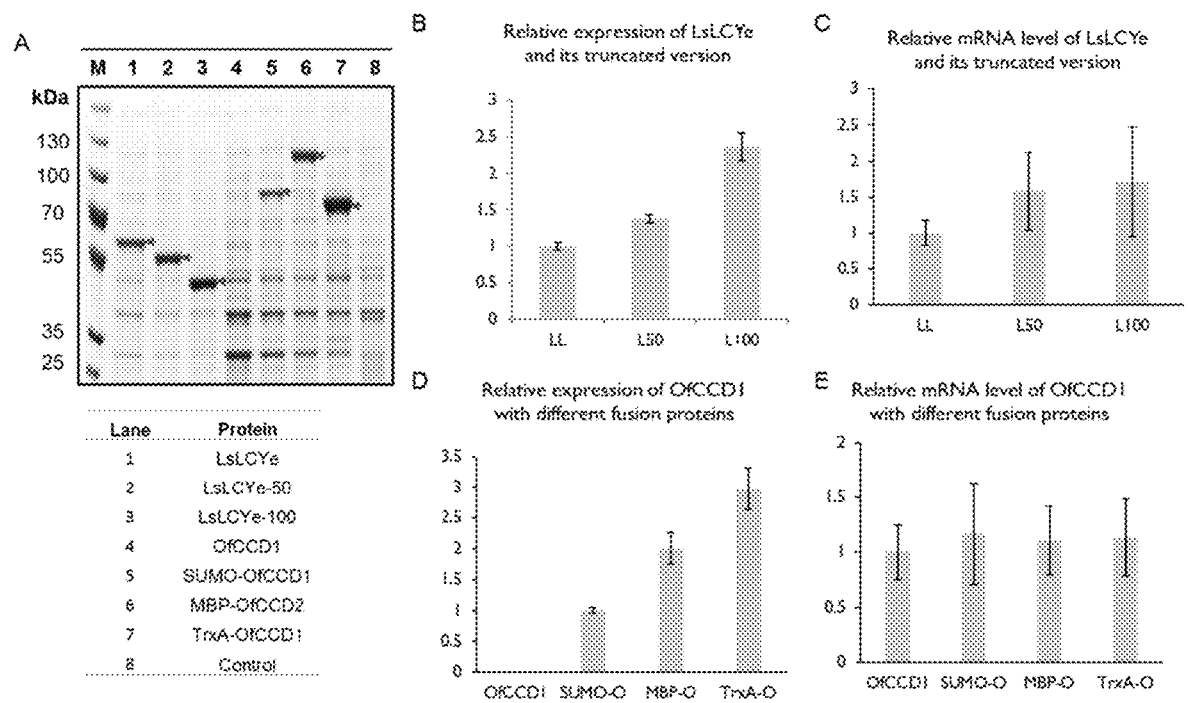
FIG. 7 shows a protein and mRNA expression analysis of LsLcyE and OfCCD1 with N-terminal modifications. (A) SDS-PAGE gel image of the whole-cell protein expression of LsLcyE and OfCCD1 with various N-terminal modifications. The proteins-of-interest were indicated with blue arrow. Lane 1: $E.\ coli$ cells with overexpressed LsLCYe. Lane 2: $E.\ coli$ cells with overexpressed Δ50-LsLCYe (L50). Lane 3: $E.\ coli$ cells with overexpressed Δ100-LsLCYe (L100). Lane 4: $E.\ coli$ cells with overexpressed OfCCD1. Lane 5: $E.\ coli$ cells with overexpressed SUMO-OfCCD1 (SUMO-O). Lane 6: $E.\ coli$ cells with overexpressed MBP-OfCCD1 (MBP-O). Lane 7: $E.\ coli$ cells with overexpressed TrxA-OfCCD1 (TrxA-O). Lane 8: $E.\ coli$ cells without any overexpression (control). Quantitative analysis of the overexpressed protein yield was based on the band intensity on SDS PAGE gel. (B) LsLCYe expression with various N-terminal truncations. (C) mRNA expression level of LsLCYe and its truncated version. (D) OfCCD1 expression with different fusion partners. (E) mRNA expression level of OfCCD1 with different fusion proteins. The relative fold change of protein expression was normalized by the expression of LsLCYe (B and C) and SUMO-OfCCD1 (D and E). The results were the average of triplicates with standard error bar shown.

Structural prediction by Phobius showed a likely membrane interaction region ($104^{th}$-$128^{th}$ amino acids) in the LsLCYe enzyme and a weak signal peptide region ($1^{st}$-$30^{th}$ amino acids). Modifications of N-terminal residues involved in membrane interactions and signal peptide coding regions have previously been reported to enhance solubility and activity of recombinant protein. Therefore, the truncation of the N-terminus sequences involved in anchoring to membrane was examined to determine if it would increase the catalytic efficiency of LsLCYe. A series of N-terminal truncated LsLCYe was constructed by systematically removing 50 residues at a time using the truncate cross-lapping in vitro assembly method. The enzymatic expression level was increased by ~40% when the first 50 amino acids (FIGS. 7A and B) were removed, with a concomitant greater than two-fold increase in ε-carotene (>40 mg/L, 5500 ppm and 80% of final products) production (FIG. 6, 121+L50 strain). Remarkably, removing the first 100 residues (FIG. 6, 121+L100 strain) led to an increase in the protein concentration by ~140% (FIGS. 7A and B). However, the cyclase activity was completely lost. In order to better understand how truncation affected LsLCYe expression, the transcription level and mRNA secondary structure of truncated LsLCYe and its native form were compared. The results indicated that increased expressions of truncated LsLCYe did not appear to be due to significant increases in mRNA expressions (FIG. 7C) nor modifications in secondary mRNA structures.

In order to demonstrate the broader utility of this modular approach, other apocarotenoids were produced by replacing the LCYe enzyme with the expression of lycopene beta cyclase (or crtY) from *Pantoea ananatis*. Unlike LsLCYe, the native lycopene beta cyclase was highly active and converted greater than 70% of lycopene into β-carotene (65 mg/L), with residual amount of lycopene (24 mg/L) (crtY strain in FIG. 15).

Production of Apocarotenoids by "Plug-n-Play"

Example 4. Optimization of α-Ionone Production

Figure 8:
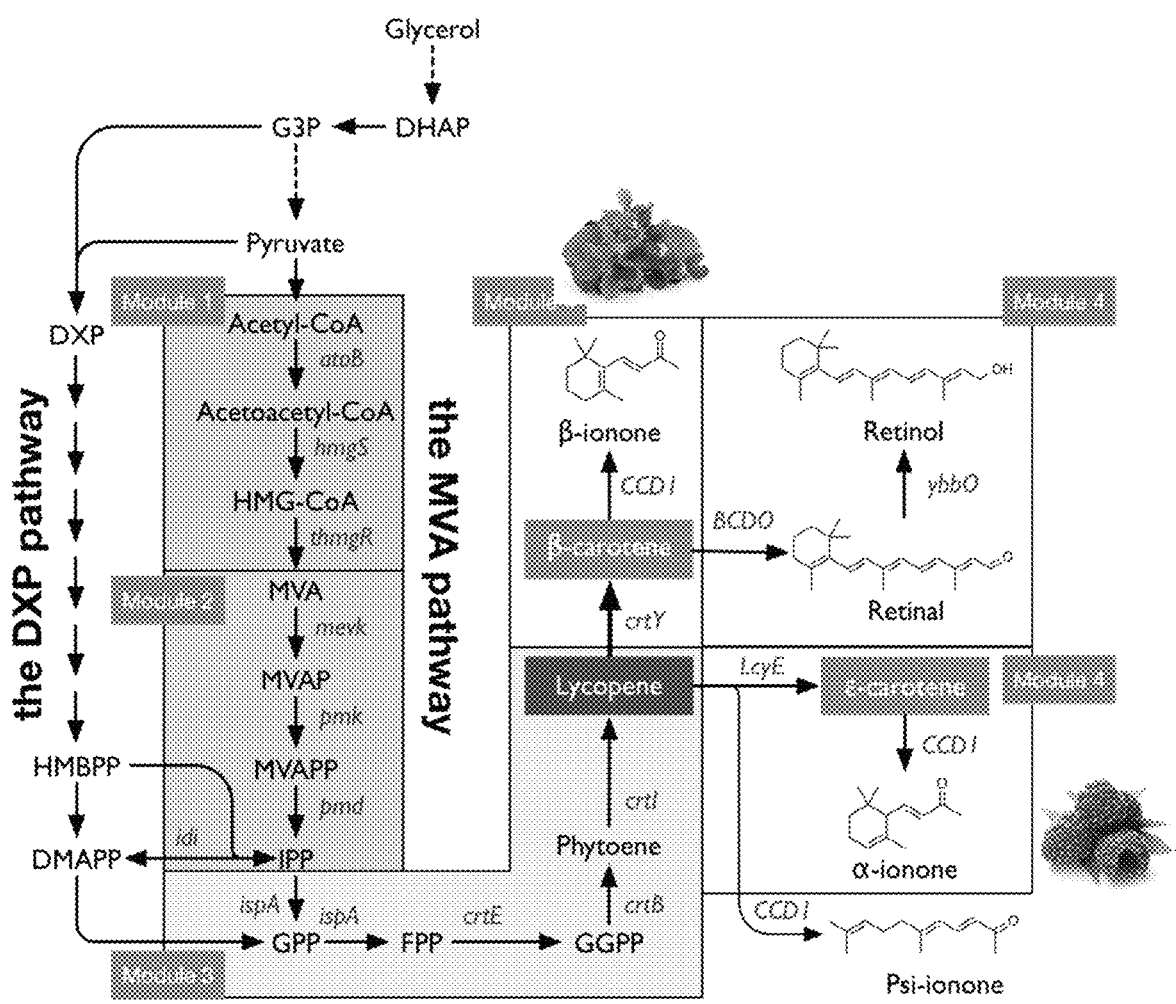
FIG. 8 is a schematic diagram of biosynthetic pathway of apocarotenoids (e.g. α, β-ionone and retinoids). The biosynthetic pathway was grouped into four major modules: the upstream MVA pathway (Expression module 1), the downstream MVA pathway (Expression module 2), the lycopene pathway (Expression module 3) and the apocarotenoid pathway (Expression module 4). The genes expressed encode the following enzymes: atoB, Acetoacetyl-CoA thiolase; hmgS, HMG-CoA synthase; thmgR, truncated HMG-CoA reductase; mevk, mevalonate kinase; pmk, phosphomevalonate kinase; pmd, mevalonate pyrophosphate decarboxylase; idi, IPP isomerase; ispA, FPP synthase; crtE, GGPP synthase; crtB, phytoene synthase; crtI, phytoene desaturase; LCYe, lycopene epsilon-cyclase; crtY, lycopene beta-cyclase; CCD1, carotenoid cleavage dioxygenase; BCDO (or blh), β-carotene dioxygenase; ybbO, NADP+-dependent aldehyde reductase. Abbreviation for the compounds: G3P, D-glyceraldehyde-3-phosphate; DHAP, Dihydroxyacetone phosphate; HMG-CoA, 3-hydroxy-3-methyl-glutaryl-coenzyme A; MVA, mevalonate; MVAP, phosphomevalonate; MVAPP, diphosphomevalonate; IPP, isopentenyl pyrophosphate; DMAPP, dimethylallyl pyrophosphate; HMBPP, (E)-4-Hydroxy-3-methyl-but-2-enyl pyrophosphate; GPP, geranyl pyrophosphate; FPP, farnesyl pyrophosphate; GGPP, geranylgeranyl pyrophosphate. Dashed arrow indicates multiple enzymatic steps.

By modular approach, carotenoid cleavage oxygenase(s) can be added to the fourth expression module to produce various apocarotenoids (FIG. 8). LsLCYe with N-terminus 50 amino acids truncated (ΔN50-LsLCYe) was further explored for α-ionone production. It has been demonstrated previously that CCD1 from *Osmanthus fragrans* (OfCCD1) can cleave carotene at C9-C10 position to produce both the α- and β-ionone. Thus, OfCCD1 enzyme was overexpressed in ε-carotene strains (121-LL and 121-L50 in FIG. 6). However, even with enhanced availability of ε-carotene in strain 121-L50-O, the amount of α-ionone detected was less than 500 µg/L (FIG. 9A, insert). As previously noted, lycopene and ε-carotene were the main intermediates accumulated in the LsLCYe and ΔN50-LsLCYe overexpressed strains, respectively (FIG. 9B). SDS-PAGE analysis showed that hardly any OfCCD1 protein was observed 24 h after induction (FIGS. 7A and D), even though mRNA was well detected (FIG. 7E). The results indicated that OfCCD1 expression may be limited by insufficient translation, consistent with previous studies on other CCD1 overexpression.

Figure 9:
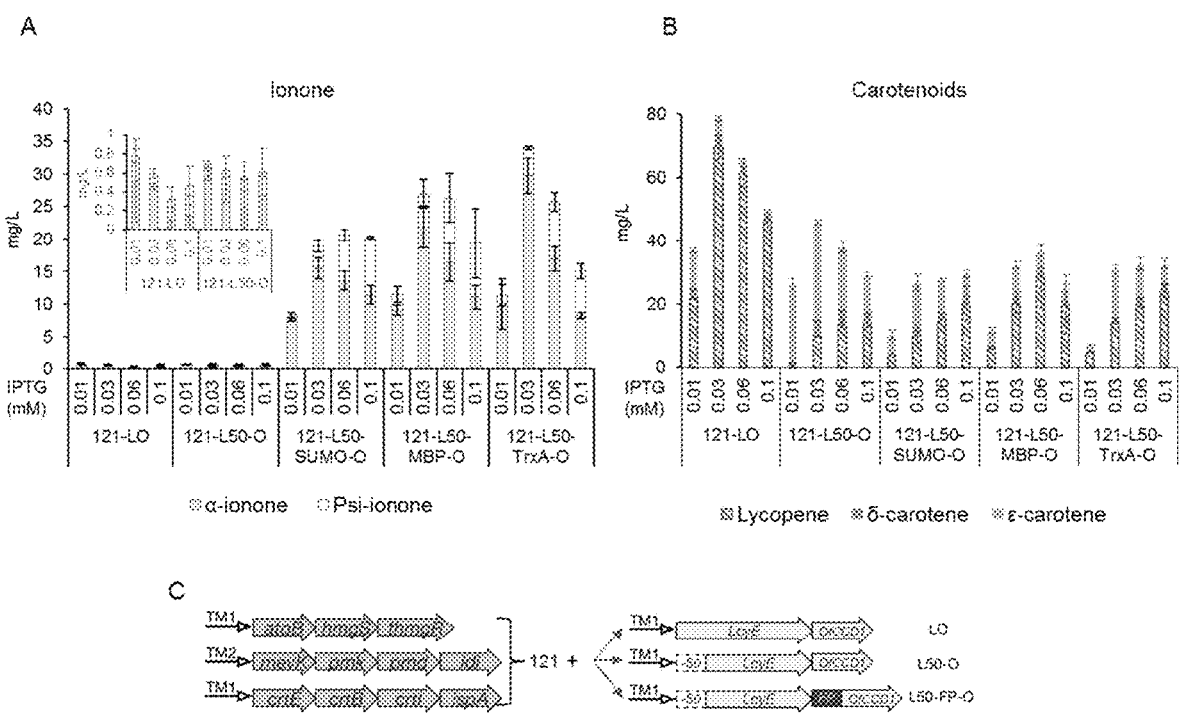
FIG. 9 shows the production of α-ionone in the ε-carotene accumulating E. coli strain. (A) Optimization of CCD1 with N-terminal fusion partners (FP), a figure insert with a different y-axis scale was supplemented to compare the ionone titers of strains 121-LO and 121-L50-O. (B) Intracellular carotenoids that remained uncleaved. (C) An illustration of promoters and regulated genes for different strains. The abbreviations are as follows. LO, LsLCYe and OfCCD1 were expressed in a polycistronic manner on the same plasmid; L50-O, LsLCYe enzyme with the first 50 amino acids removed (L50) and OfCCD1 were expressed in a polycistronic manner. L50-SUMO-O, L50 and SUMO-fused OfCCD1 were co-expressed. L50-MBP-O, L50 and MBP-fused OfCCD1 were co-expressed. L50-TrxA-O, L50 and TrxA-fused OfCCD1 were co-expressed.
Figure 10:
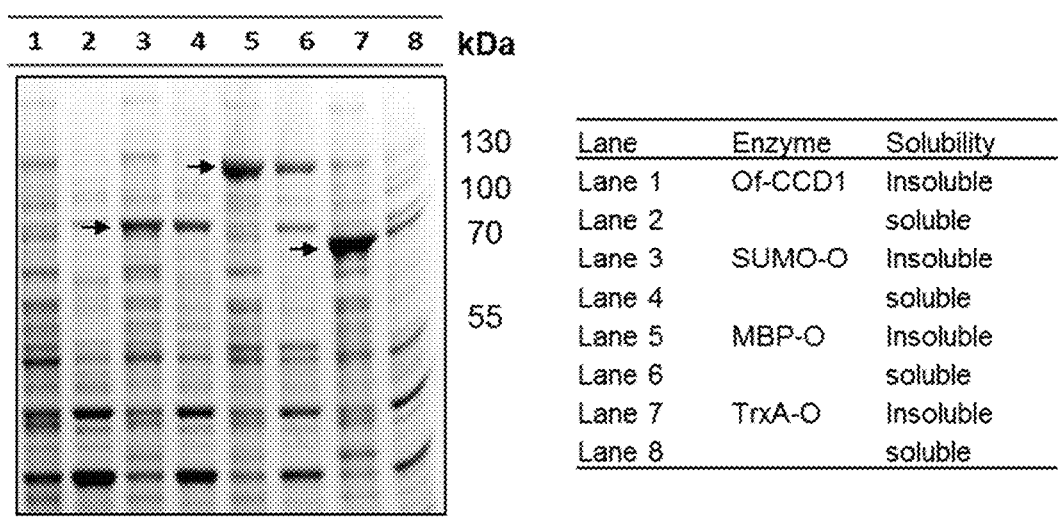
FIG. 10 shows the protein solubility of OfCCD1 with N-terminal modifications. The proteins of interest were indicated with arrow. Lane 1: insoluble OfCCD1. Lane 2: soluble OfCCD1. Lane 3: insoluble SUMO-OfCCD1. Lane 4: soluble SUMO-OfCCD1. Lane 5: insoluble MBP-OfCCD1. Lane 6: soluble MBP-OfCCD1. Lane 7: insoluble TrxA-OfCCD1. Lane 6: soluble TrxA-OfCCD1.

Literature suggested that fusion with glutathione-S-transferase (GST) would significantly increase expression and solubility of CCD1 in *E. coli*. Thus, the fusion partners were examined for improvements in the functional expression of OfCCD1. Three commonly used N-terminal fusion partners, small ubiquitin-like modifier (SUMO) protein, maltose binding protein (MBP) and thioredoxin (TrxA) were tested. OfCCD1 when fused with the three fusion partners significantly increased the titers of α-ionone (FIG. 9A). Among them, the strain with TrxA-fused OfCCD1 (or TOfCCD1) was able to produce 29.7 mg/L α-ionone with low induction (0.03 mM IPTG), which is more than 50-fold improvement (FIG. 9A). To study the underlying mechanism of fusion partners, the protein expression was further investigated by denaturing SDS-PAGE gel. Without fusion partner, OfCCD1 was barely detectable (FIGS. 7A and D). In contrast, OfCCD1 enzymes fused with SUMO, MBP and TrxA were well expressed. The relative protein band intensities of SUMO-, MBP- and TrxA-fused OfCCD1 were well correlated with their corresponding α-ionone production in FIG. 9A. For example, TOfCCD1 expressing strain had the best expression and produced the highest amount of α-ionone. The effects of fusion partners on solubility of OfCCD1 were further investigated. All the fused CCD1 have clear soluble fractions (FIG. 10), however, there was no clear correlation between α-ionone production and solubility of SUMO-, MBP- and TrxA-fused OfCCD1. As transcription and mRNA secondary structure remained relatively similar, the increased expression of OfCCD1 was likely to be due to an enhancement in translation efficiency or increase in protein stability. Interestingly, even with the highest ionone producer strain (FIG. 9, 121-L50-TrxA-O strain with 0.03 mM IPTG), both ε-carotene and lycopene (~30 mg/L total carotenoids) were still accumulated to the similar levels as α-ionone (FIG. 9B), suggesting that α-ionone yield could be further improved. Hence, a progressive improvement in the production of α-ionone from 500 µg/L to 29 mg/L was achieved.

Figure 11:
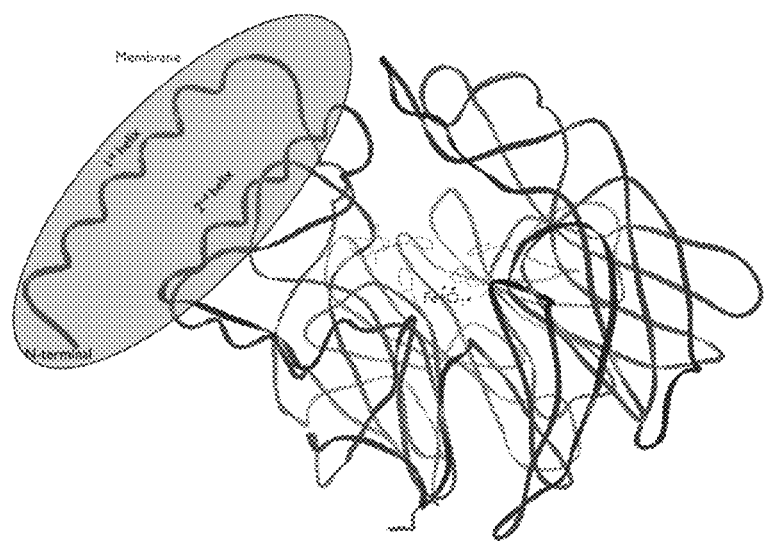
FIG. 11 shows the homology modelling of OfCCD1 based on the crystal structure of viviparous14 from Zea mays (PDB: 3NPE). The two membrane interacting helices are labelled. The membrane is represented by the shaded area. The co-factor, $Fe^{2+}$ and oxygen are labeled.
Figure 12:
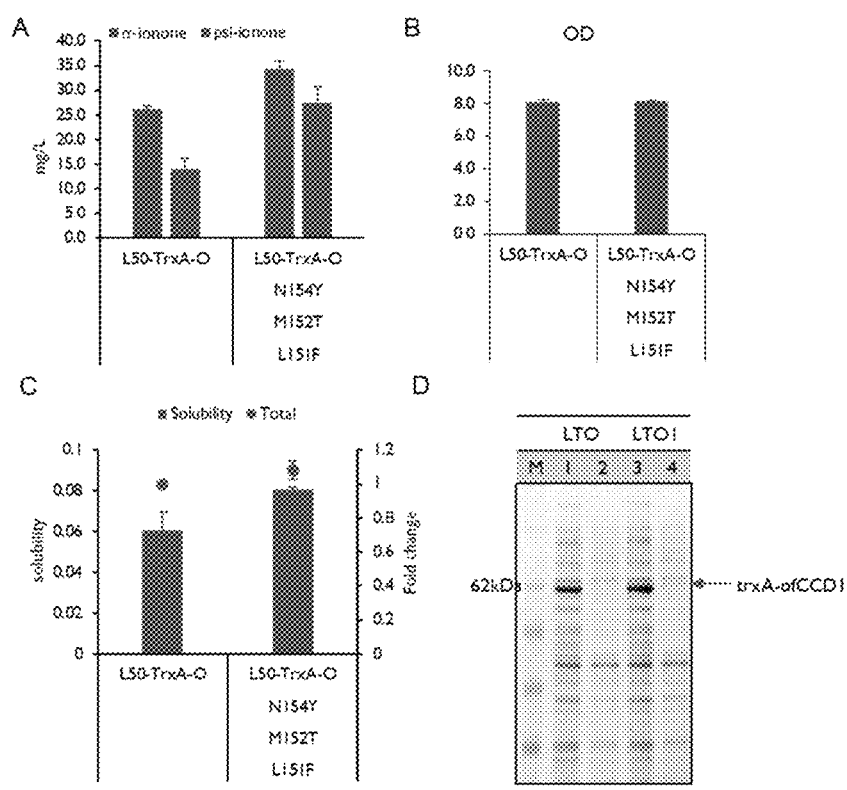
FIG. 12 shows the engineering of the second membrane interacting helix of OfCCD1. (A) A comparison of the titer of α-ionone and psi-ionone between the wide type ofCCD1 and engineered ofCCD1 with mutations (L151F, M152T and N154Y). (B) Biomass of the engineered strain. (C) The solubility and fold change in total expression of TrxA-fused wide-type OfCCD1 and trxA-fused mutant OfCCD1. (D) The SDS PAGE gel image of TrxA-fused wide-type OfCCD1 and trxA-fused mutant OfCCD1. Lane M, molecular marker. Lane 1, the total proteins of E. coli cell expressing trxA-fused wide-type OfCCD1. Lane 2, the soluble proteins of E. coli cell expressing trxA-fused wide-type OfCCD1. Lane 3, the total proteins of E. coli cell expressing trxA-fused mutant OfCCD1. Lane 4, the soluble proteins of E. coli cell expressing trxA-fused mutant OfCCD1.

To further improve the α-ionone yield, homology modelling was used to predict the 3D structure of OfCCD1 (FIG. 11). There are two membrane-interaction helices based on the OfCCD1 model. The first helix is located at the N-terminal of the protein, and the second helix is found within the sequence (F148-I167). Sequence alignment indicated the main discrepancies occurred at leucine-151, methionine-152, asparagine-154, and isoleucine-167 (FIG. 18). By simultaneously mutating leucine-151 to phenylalanine, methionine-152 to threonine and asparagine-154 to tyrosine, the α-ionone titer was further improved to ~35 mg/L (FIG. 12A). Protein expression analysis showed that these mutations have further improved the trxA-fused OfCCD1 expression (FIGS. 12C and D). The results highlighted that CCD enzyme engineering is critical for improving ionone production.

Figure 13:
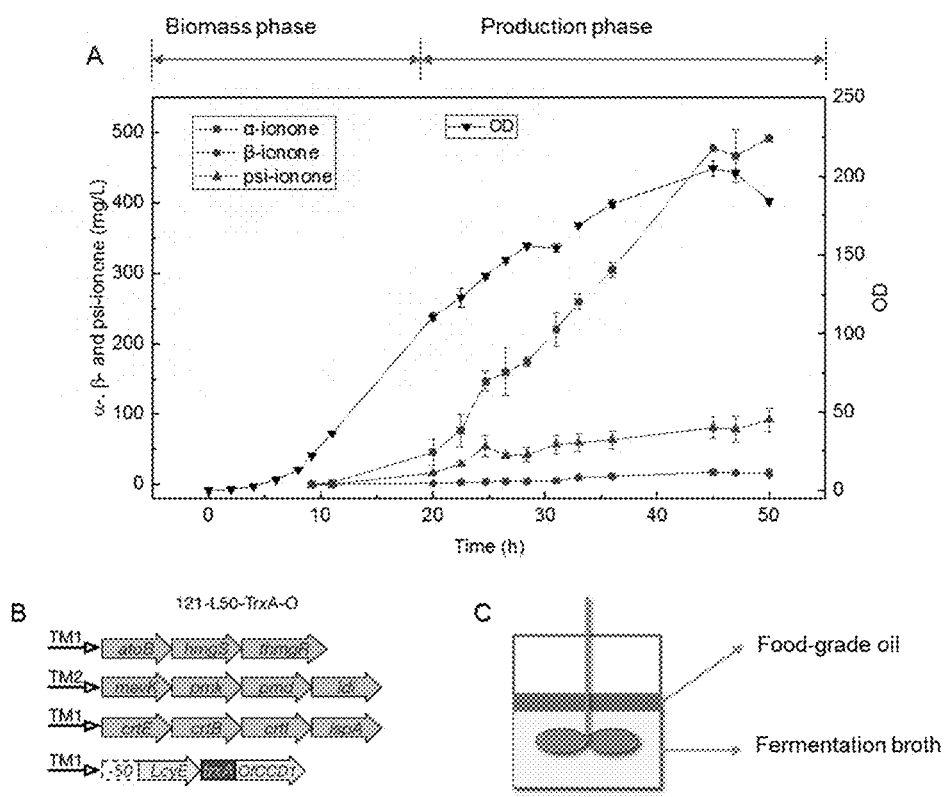
FIG. 13 shows the fed-batch fermentation of apocarotenoids. (A) Time-course profiles for ionones and biomass. (B) An illustration of promoters and regulated genes for the strain used in the fed-batch fermentation. Separated by induction, the process consisted of two major phases, biomass phase accumulating only biomass and production phase that simultaneously produced ionone and biomass. Isopropyl myristate was used as organic layer to extract the α-, β- and psi-ionone. (C) An illustration of the in situ separation of apocarotenois in bioreactor. Food-grade coconut oil (or soybean oil etc) as organic layer to extract the α-, β- and psi-ionone. Chemically defined media without any amino acid and vitamin was used to reduce the cost of medium.

Next, the performance in fed-batch fermentation was tested using the best α-ionone producing strain (121-L50-TrxA-O strain). As α-ionone is volatile, isopropyl myristate was used to entrap the compound during fermentation. As shown in FIG. 13, about 480 mg/L of α-ionone was produced within 48 h. In sum, a 1000-fold increase in the α-ionone production from initial 500 µg/L to 480 mg/L was achieved. Thus, the α-ionone titer achieved in this study is about 1428 times higher than previously reported.

Figure 14:
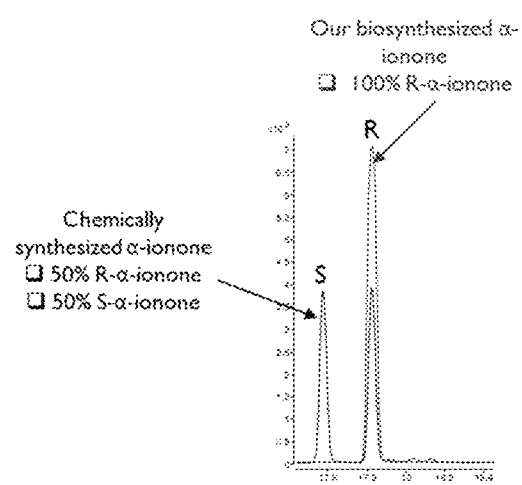
FIG. 14 shows the chirality analysis of α-ionone. The product is 100% R-enantiomer of α-ionone and identical to natural α-ionone. In contrast, the chemically synthesized ionone is a mixture of 50% R-enantiomer and 50% S-enantiomer.

Furthermore, the produced α-ionone was subjected to chirality check and found to be 100% R-enantiomer of α-ionone (FIG. 14), identical to natural α-ionone. In contrast, the chemically synthesized ionone is a mixture of 50% R-enantiomer and 50% S-enantiomer. More importantly, different enantiomers of ionone have different odors and potential different activities. The result clearly showed the advantage of biosynthesis through the "plug-n-play" platform over chemical synthesis.

Example 5. Optimization of β-Ionone Production

Figure 16:
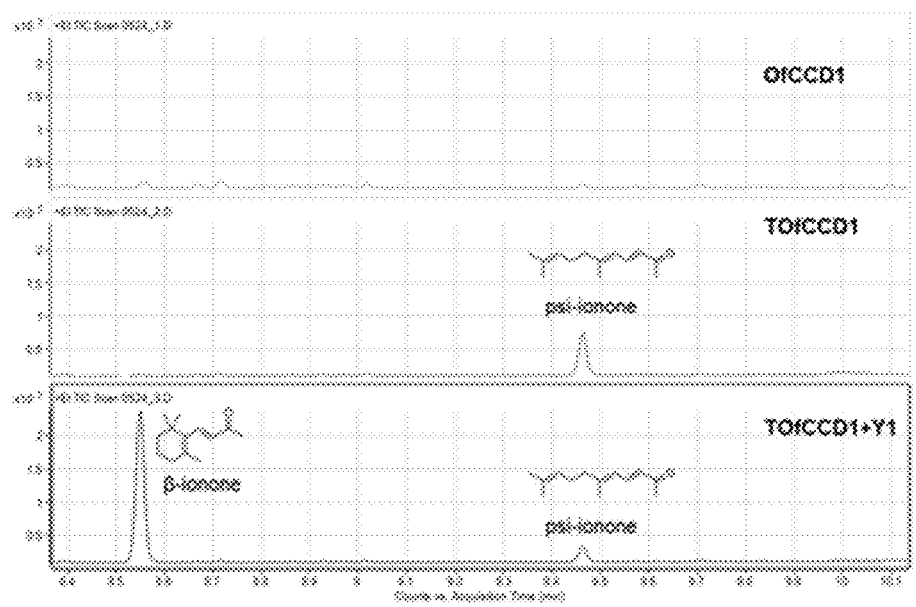
FIG. 16 shows the GC-chromatograms of products in Of, TOf and TOf+Y strain.
Figure 17:
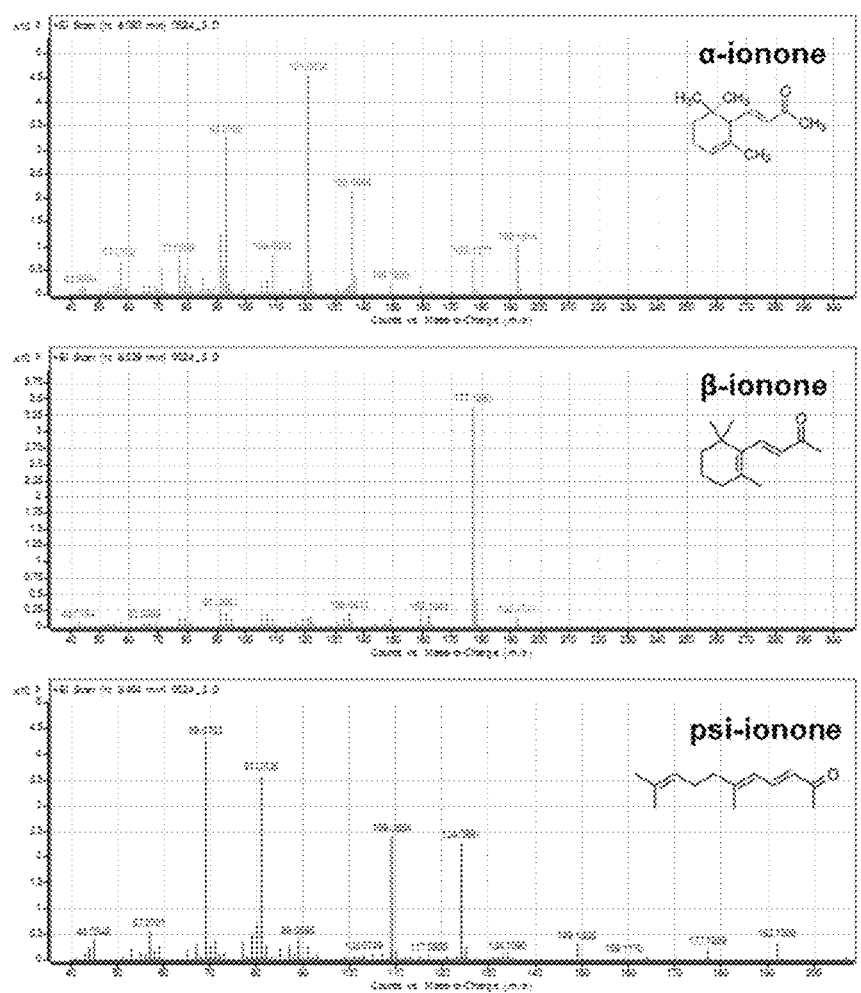
FIG. 17 shows the mass spectra of α, β and psi-ionone.

To demonstrate the broader utility of this modular approach, other apocarotenoids were produced by co-expressing carotenoids cleavage dioxygenase with lycopene beta cyclase (or crtY) from *Pantoea ananatis*. The β-ionone production with wild-type OfCCD1 expressing strain (Of strain) was 140 µg/L, corresponding to merely less than 1% conversion yield from β-carotene (FIG. 15). As the N-terminal TrxA fused OfCCD1 (TOfCCD1) improved α-ionone (FIG. 9), the possibility that it may similarly improve β-ionone production was tested. Disappointingly, TOfCCD1 expression did not result in a significant increase in the production of β-ionone (FIG. 15A). Instead, another major peak at 9.46 min was detected in the GC chromatogram (FIGS. 16 and 17). This peak was predicted to be psi-ionone with the National Institute of Standards and Technology (NIST) mass spectrum library and further validated with authentic standard of psi-ionone. The expression of TOfCCD1 resulted in a 37-fold increase in psi-ionone production from ~0.4 to ~14.6 mg/L. Noteworthy, psi-ionone was also produced by the α-ionone production strain, although it was a minor product (FIGS. 9A and 12A). Hence, it appeared that lycopene was also cleaved by TOfCCD1 and produced psi-ionone (FIG. 8), consistent with the observation that certain types of CCD1 could convert lycopene to psi-ionone or 6-methyl-5-hepten-2-one (MHO). In addition, it was observed that no β-carotene but large amount of lycopene accumulated in TOfCCD1 expressing strain (TOf strain, FIG. 15B). One possible reason could be that lycopene was preferentially converted by TOfCCD1 rather than cyclized by the lycopene beta cyclase in exponential phase.

As large amount of lycopene and lycopene-derived psi-ionone were produced in the TOf strain, it was hypothesized that increasing the gene dosage of crtY (TOf+Y strain) may have two potential benefits. Firstly, it may increase the carbon fluxes from lycopene to β-carotene and hence increase β-ionone production. Secondly, the production of psi-ionone may be reduced by the decrease in the availability of intracellular lycopene. To test the hypothesis, crtY was firstly inserted into the first expression module of our system, atoB-hmgS-hmgR, resulting in a new operon, crtY-atoB-hmgS-hmgR (illustrated in FIG. 15). As the plasmids used in the study are about 10 copies per cell, the insertion increased the crtY copy number from 10 to 20 copies per cell. Interestingly, gene dosage of crtY effectively resulted in more lycopene converted to β-carotene, hence, from undetectable amount of β-carotene (TOf strain, FIG. 15) to a significant yield of 42.4 mg/L (TOf+Y strain, FIG. 15). Consequently, the titer of β-ionone was significantly increased from 0.3 to 20.9 mg/L, and psi-ionone was decreased from 14.6 to 4.4 mg/L (FIG. 15), indicative of a higher carbon flux diverted into β-ionone production through β-carotene.

Figure 19:
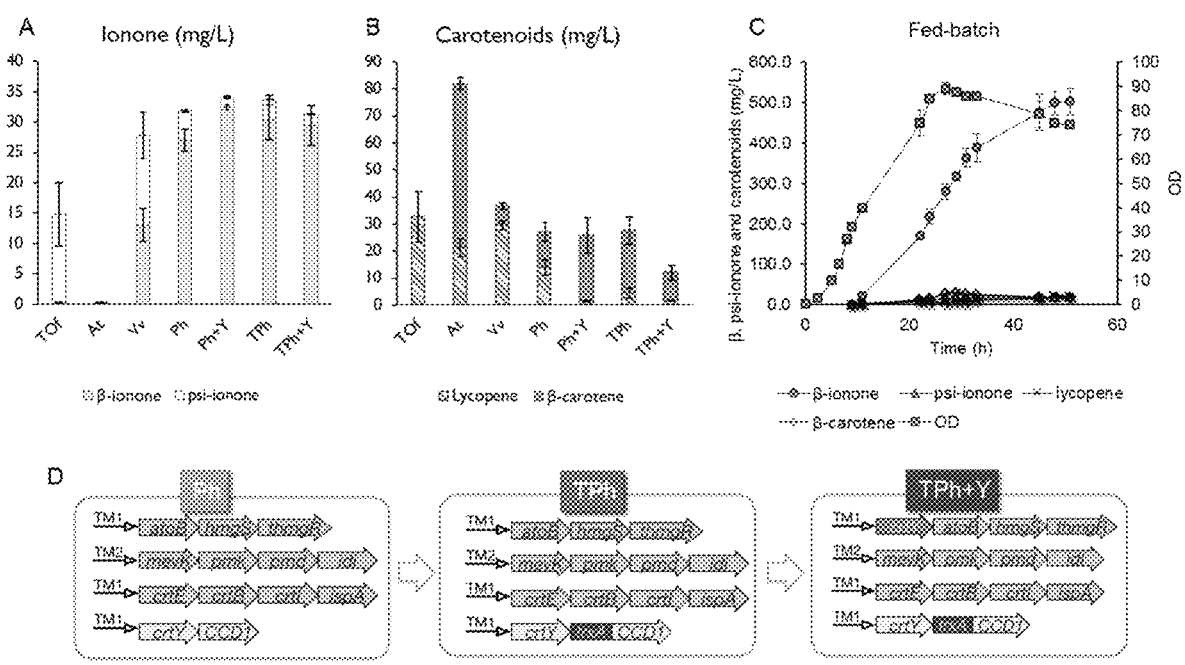
FIG. 19 demonstrates the screening of CCDs with higher selectivity. (A) Ionone production using different CCDs. (B) Carotenoids accumulated in E. coli cells with different CCDs. In TOf, At, Vv, Ph, TPh strain, the operon/gene crtY-TrxA-OfCCD1, crtY-AtCCD1, crtY-VvCCD1, crtY-PhCCD1 and crtY-TrxA-PhCCD1 were expressed, respectively. In Ph+Y and TPh+Y strain, additional copy of crtY gene was supplemented in the p15A-spec vector. It was found that PhCCD1 had higher selectivity for β-carotene versus lycopene than VvCCD1 and OfCCD1, thus produced higher titer of ionone and lower amount of psi-ionone. (C) Fed-batch fermentation of β-ionone with strain TPh+Y. (D) An illustration of promoters and regulated genes for different strains.

Although supplementation of crtY markedly improved β-ionone production, there was still 4.4 mg/L of psi-ionone produced. To maximize the β-ionone production and minimize by-product/intermediates formation, CCD with higher selectivity for β-carotene was screened. Another three CCD1 enzymes, from *Arabidopsis thaliana* (AtCCD1), *Vitis vinifera* (VvCCD1) and *Petunia* hybrid (PhCCD1) were tested (FIG. 18). All CCD1 enzymes used in this study are shown in Table 4. With the expression of wild-type AtCCD1, VvCCD1 and PhCCD1, β-ionone was produced at 0.1, 13.0 and 27.0 mg/L, respectively, accompanied by 0.2, 14.8 and 4.8 mg/L psi-ionone, respectively (FIG. 19A). The data suggested that wild-type VvCCD1 and PhCCD1 had higher activities in *E. coli* than AtCCD1 and OfCCD1. In addition, PhCCD1 also had higher selectivity for β-carotene than VvCCD1 and TOfCCD1. Nevertheless, there were still 13.3 mg/L β-carotene and 13.8 mg/L lycopene accumulated in the PhCCD1 expressing strain (FIG. 19B). The fusion of TrxA to PhCCD1 and supplementation of additional copy of crtY was next investigated. With additional supplementation of crtY (Ph+Y strain), the β-ionone titer increased from 27 to 32.4 mg/L and psi-ionone titer decreased from 4.8 to 1.6 mg/L. Concomitantly, β-carotene production increased from 13.3 (Ph strain) to 24.3 (Ph+Y strain) mg/L and lycopene production decreased from 13.8 to 1.5 mg/L. However, the fusion of TrxA (TPh strain) merely resulted in a moderate increase in β-ionone production from 27 to 30.4 mg/L and a slight decrease in psi-ionone production from 4.8 to 3.2 mg/L. Furthermore, there was no synergistic benefit with the combination of crtY supplementation and TrxA fusion (TPh+Y strain, FIG. 19). Collectively, the results suggested that unlike OfCCD1, native PhCCD1 activity was sufficiently efficient in converting β-carotene to β-ionone. In sum, the β-ionone production from initial 140 µg/L to 32.4 mg/L was improved, a ~230-fold increase in tubes and flasks over a period of 24 h. Further in fed-batch fermentation, ~500 mg/L of β-ionone was produced with Ph+Y strain (FIG. 19C), which was about 3700-fold increase over that of the initial strain.

Table 4 summarizes the CCD1 enzymes in this study.

| Entry | Enzymes | Organisms |
|---|---|---|
| O65572 | AtCCD1 | *Arabidopsis thaliana* (Mouse-ear cress) |
| U3M7F6 | VvCCD1 | *Vitis vinifera* (Grape) |
| D4QE74 | OfCCD1 | *Osmanthus fragrans* |
| Q6E4P3 | PhCCD1 | *Petunia hybrida* (Petunia) |

Figure 20:
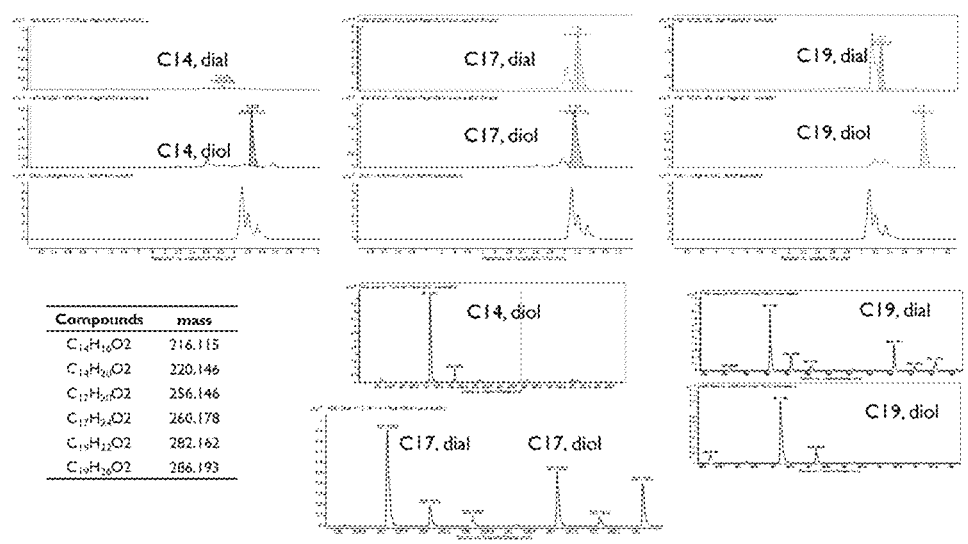
FIG. 20 shows the mass spectra of dialdehydes and dialcohols produced in the fermentator. C17 and C19 of dialdehydes and dialcohols were detected, but not C14.

The organic phase from the bioreactor was yellow in color. To identify the yellow compound(s), ultra performance liquid chromatography coupled with time-of-flight mass spectrometry analysis was carried out. A few dialdehydes (C17 and C19) and alcohols were identified (FIG. 20). These are the by-products due to the non-specific cleavage of PhCCD1. To circumvent the problem, screening for a more specific CCD would was carried out. Since CCD4 has demonstrated remarkable improvement in the substrate and product specificity, we have screened several CCD4 enzymes listed in Table 5, and found that PpCCD4 is most active against β-carotene, and CmCCD4 is most active against ε-carotene (FIG. 21).

Table 5 summarizes the CCD2 and CCD4 enzymes in this study.

| CCD enzymes | Organisms |
|---|---|
| CaCCD2 | *Crocus angustifolius* |
| CsCCD2 | *Crocus sativus* |
| AtCCD4 | *Arabidopsis thaliana* |
| BoCCD4b | *Bixa orellana* |
| CmCCD4 | *Chrysanthemum morifolium* |
| CsCCD4a | *Crocus sativus* |
| MaCCD4 | *Musa acuminata* AAA Group |
| MdCCD4 | *Malus domestica* |
| OfCCD4 | *Osmanthus fragran* |
| PpCCD4 | *Prunus persica* |
| RdCCD4 | *Rosa damascena* |
| VvCCD4a | *Vitis vinifera* |

Example 6. Optimization of Retinoids Production

Figure 22:
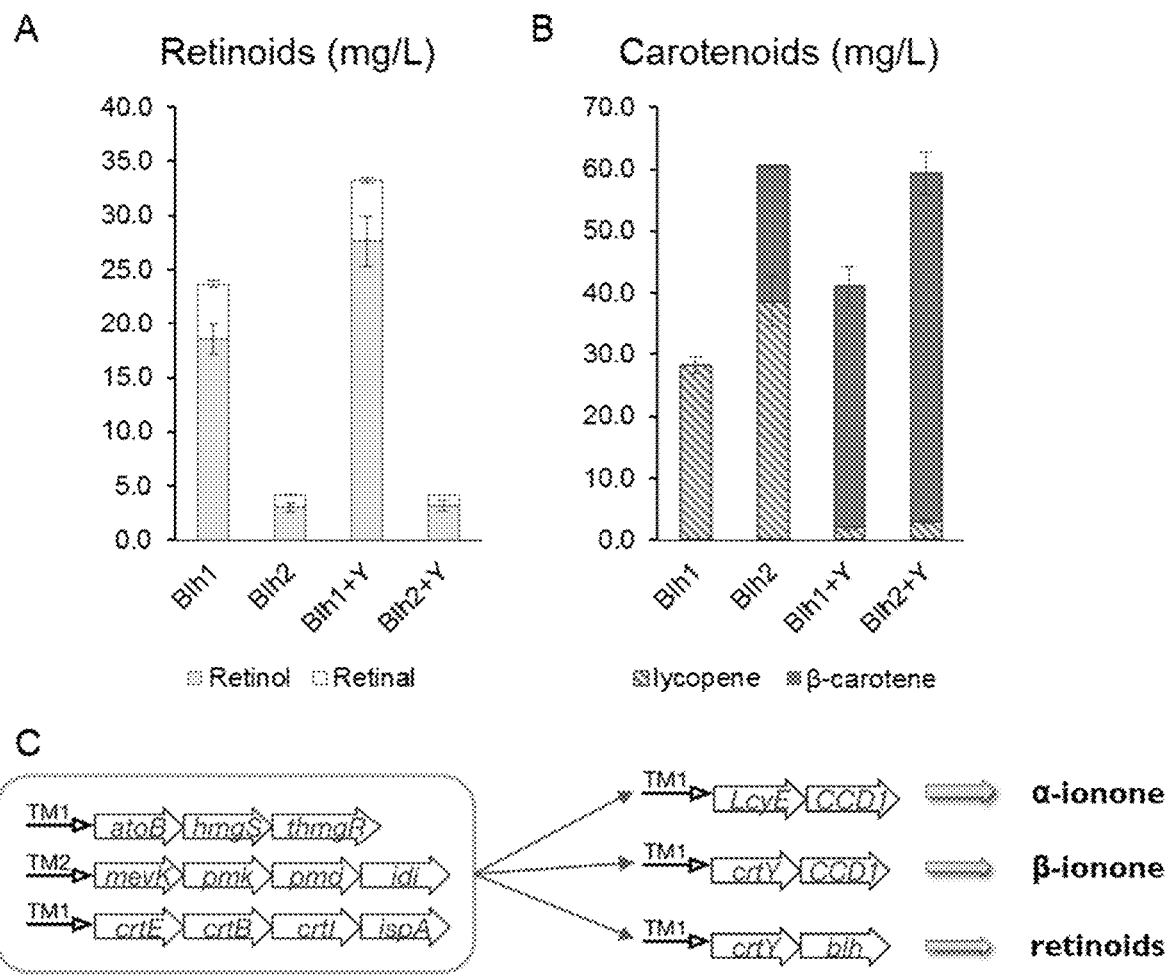
FIG. 22 shows the production of retinoids in the modularized system. (A) Retinoid production using different blh genes and increased gene copy of crtY. (B) Carotenoids accumulated in different E. coli cells. To produce other apocarotenoids, we could merely replace the CCD1 enzyme with other corresponding carotenoid cleavage oxygenases. Here, we used BCDO (blh) to produce retinoids. (C) A summary illustration of the modular system for the production of different apocarotenoids.

Retinoids are biosynthesized by cleaving β-carotene at C15-C15' position. To further illustrate the utility of the "plug-n-play" system to produce other apocarotenoids, CCD1 gene was replaced with two blh genes (BCDO enzyme, FIG. 8), from Uncultured marine bacterium HF10_19P19 (blh1) and Uncultured marine bacterium 66A03 (blh2). Without any optimization of the upstream pathway, the "plug-n-play" system produced 18.5 mg/L retinol and 5.1 mg/L retinal in the blh1 strain and 3.0 mg/L retinol and 1.1 mg/L retinal in blh2 strain (FIG. 22A). In blh1 strain, lycopene accumulated (28.2 mg/L) but no β-carotene was detected (FIG. 22B). Thus, it was hypothesized that retinoid production was limited by lycopene beta-cyclase instead of BCDO in blh1 strain. As expected, the co-expression of additional crtY gene (blh1+Y) increased retinoid production (from 23.6 to 33.2 mg/L). As for blh2 strain, retinoid production was likely to be limited by the activity of BCDO instead of lycopene beta-cyclase, as the increase in crtY gene dosage failed to improve the retinoid production despite that >90% lycopene was converted into β-carotene (FIG. 22). It is worth noting that in the retinoid-producing strains, the ybbO gene, predicted as an oxidoreductase in *E. coli* and validated experimentally with high retinol dehydrogenase activity (Genbank Accession ID is ECD_00444, FIG. 8), was not overexpressed but greater than 80% of retinal was converted into retinol. While the underlying mechanism was unknown, it could be due to the relatively high intracellular expression of ybbO enzyme or other unknown endogenous proteins with retinol dehydrogenase activity. The retinoid and ionone results suggested that this "plug-n-play" system is versatile and will be useful for the production of many apocarotenoids which share a common upstream pathway (FIG. 22C).

Discussion

Modular metabolic engineering has been successfully applied to rationally improve small molecule production by microbial cell factories. It is a powerful approach to reduce the parameter optimization space and allow sequential optimization of subsets of expression modules before amalgamating with the full pathway. Generally, as expression module number increases, the accuracy of pathway optimization will improve but the full combination will also increase exponentially. Thus, a balanced expression module number has to be decided. As described herein, the multi-gene pathway containing 13 genes was cast into 4 different expression modules: upstream mevalonate pathway (expression module 1), downstream mevalonate pathway (expression module 2), lycopene biosynthetic pathway (expression module 3) and apocarotenoids biosynthetic pathway (expression module 4). By optimizing the first three metabolic expression modules with EDASPO approach, a stable parental strain that accumulated high content of lycopene was obtained (strain 121 in FIG. 6). Subsequently, the fourth expression module that carried lycopene cyclase and CCD was introduced to produce various apocarotenoids. Having the apocarotenoid expression module independent from the rest of the expression modules offers three major advantages over non-modular approaches. Firstly, it minimizes the potential negative effects on the upstream system (the mevalonate pathway and lycopene biosynthetic pathway). Secondly, it significantly simplifies the strain engineering workload. As the upstream system was optimized and remained efficient, engineering efforts could be focused on the downstream apocarotenoid biosynthesis expression module. Lastly, it makes the system a 'plug-n-play' chassis for the production of valuable apocarotenoids. As such, 'plugging' lycopene cyclase (LCYe or crtY) and CCD1 produces α- or β-ionone and 'plugging' crtY and blh produces retinol. More importantly, similar titers of the apocarotenoids were obtained in flasks (FIGS. 9, 15, 19 and 22) indicating the robustness of this modular system.

Collectively, these results demonstrate that modulating key protein expression is essential for the heterologous biosynthesis of apocarotenoids in $E.$ $coli$. Broadly, this highlights the benefits of combining protein engineering and modular pathway design for the overproduction of valuable chemicals.

The recent changes in the regulation of natural ingredient labelling have resulted in the increase in demand of natural flavours and fragrances. Consequently, there are growing interests in engineering microbes to produce the ingredients from renewable resources. However, the complex metabolic characteristics of apocarotenoid pathway have hampered the development of highly efficient microbial processes. Advantageously, the present disclosure provides modular metabolic engineering and enzyme engineering strategies that were systematically applied to effectively minimize the metabolic burden imposed by overexpression of 13 enzymes to overcome the challenge from critical enzymes of low activities. This strategy has enabled the development of a robust $E.$ $coli$ strain capable of producing unprecedented yields of α-ionone and β-ionone, demonstrating the great potential of using microbes in production of natural flavours and fragrances.

The invention claimed is:

1. A method for producing a-ionone comprising the step of expressing in an *Escherichia coli* host cell an expression module comprising an expression vector having a coding region encoding optimized a-ionone generating enzymes, the coding region being operably linked to a promoter,
wherein the optimized a-ionone generating enzymes are LcyE and CCD1 that form an operon having the structure of LcyE-CCD1, and
wherein the LcyE is obtained from *Lactuca sativa* and comprises an N-terminal truncation of 50 amino acids (ΔN50-LsLcyE), and
wherein the CCD1 is fused with an N-terminal fusion partner.

2. The method of claim 1, further comprising expressing in the host cell:
a first expression module comprising an expression vector having a first coding region encoding one or more optimized first gene products that form an operon having the structure of atoB-hmgS-thmgR, the first coding region being operably linked to a promoter;
a second expression module comprising an expression vector having a second coding region encoding one or more optimized second gene products that form an operon having the structure of mevk-pmk-pmd-idi, the second coding region being operably linked to a promoter; and
a third expression module comprising an expression vector having a third coding region encoding one or more optimized third gene products that form an operon having the structure of crtE-crtB-crtI-ispA, the third coding region being operably linked to a promoter.

3. The method of claim 1, wherein the host cell is *Escherichia coli* BL21 DE3 or *Escherichia coli* MG1655 DE3.

4. The method of claim 1, wherein the promoter is one or more of TM1, TM2 or TM3, T7 RNA polymerase promoter, a T5 RNA polymerase promoter, a T3 RNA polymerase promoter, an SP6 RNA polymerase promoter or an inducible promoter.

5. The method of claim 2, wherein the a-ionone generating enzymes and gene products are optimized by codon optimization or site-directed mutagenesis.

6. An *Escherichia coli* host cell comprising an expression module comprising an expression vector having a coding region encoding optimized α-ionone generating enzymes, the coding region being operably linked to a promoter,
   wherein the optimized α-ionone generating enzymes are LcyE and CCD1 that form an operon having the structure obtained from *Lactuca sativa* and is N-terminally truncated,
   wherein the LcyE comprises a N-terminal truncation of 50 amino acids (ΔN50-LsLcyE), and
   wherein the CCD1 is fused with an N-terminal fusion partner.

7. The *Escherichia coli* host cell of claim 6, wherein the optimized α-ionone generating enzyme is *Osmanthus fragrans* CCD1 fused with thioredoxin (TrxA).

8. The *Escherichia coli* host cell of claim 7,
   wherein the *Osmanthus fragrans* CCD1 is encoded by the sequence set forth in SEQ ID NO: 7, and comprises one or more mutations selected from the group consisting of: N154Y, M152T, and L151 F.

9. The *Escherichia coli* host cell of claim 6, further comprising:
   a first expression module comprising an expression vector having a first coding region encoding one or more optimized first gene products that form an operon having the structure of atoB-hmgS-thmgR, the first coding region being operably linked to a promoter;
   a second expression module comprising an expression vector having a second coding region encoding one or more optimized second gene that form an operon having the structure of mevk-pmk-pmd-idi, the second coding region being operably linked to a promoter; and
   a third expression module comprising an expression vector having a third coding region encoding one or more optimized third gene products that form an operon having the structure of crtE-crtB-crtl-ispA, the third coding region being operably linked to a promoter.

10. The *Escherichia coli* host cell of claim 6, wherein the *Escherichia coli* is BL21DE3 or MG1655 DE3.

11. A kit for producing an expression module comprising an expression vector having a coding region encoding optimized α-ionone generating enzymes, the coding region being operably linked to a promoter, wherein the optimized α-ionone generating enzymes are ΔN50-LsLcyE and TrxA-Osmanthus fragrans CCD1 for the production of α-ionone.

12. The cyctcm kit of claim 11, further comprising:
   a first expression module comprising an expression vector having a first coding region encoding one or more optimized first gene products that form an operon having the structure of atoB-hmgS-thmgR, the first coding region being operably linked to a promoter;
   a second expression module comprising an expression vector having a second coding region encoding one or more optimized second gene products that form an operon having the structure of mevk-pmk-pmd-idi, the second coding region being operably linked to a promoter; and
   a third expression module comprising an expression vector having a third coding region encoding one or more optimized third gene products, the third coding region being operably linked to a promoter.

13. The method of claim 1, wherein the CCD1 is expressed as:
   i) a fusion protein selected from the group consisting of: TrxA-CCD1, SUMO-CCD1 and MBP-CCD1;
   ii) a TrxA-CCD1 fusion protein selected from the group consisting of: TrxA-*Osmanthus fragrans* CCD1 and TrxA-Petunia hybrid CCD1; or iii) a TrxA-Osmanthus fragrans CCD1 fusion protein, wherein the CCD1 is derived obtained from or is *Osmanthus fragrans* (OfCCD1) encoded by the sequence set forth in SEQ ID NO: 7, and comprises one or more mutations selected from the group consisting of: N154Y, M152T, and L151F.

14. The method of claim 1, further comprising screening for an expression level of a-ionone in an amount from 100-1000 mg/L in a 24 hour period.

* * * * *

UNITED STATES PATENT AND TRADEMARK OFFICE
CERTIFICATE OF CORRECTION

PATENT NO. : 11,920,137 B2  
APPLICATION NO. : 16/488504  
DATED : March 5, 2024  
INVENTOR(S) : Congqiang Zhang et al.

Page 1 of 1

It is certified that error appears in the above-identified patent and that said Letters Patent is hereby corrected as shown below:

In the Claims

At Column 35, Line 51, "a-ionone" should be -- α-ionone --.

At Column 35, Line 54, "a-ionone" should be -- α-ionone --.

At Column 35, Line 56, "a-ionone" should be -- α-ionone --.

At Column 35, Line 58, "LcyE-CCD1, and" should be -- LcyE-CCD1, --.

At Column 37, Line 6, "a-ionone" should be -- α-ionone --.

At Column 38, Line 11, "cyctcm kit" should be -- kit --.

At Column 38, Line 41, "a-ionone" should be -- α-ionone --.

Signed and Sealed this  
Twenty-fifth Day of February, 2025

Coke Morgan Stewart  
*Acting Director of the United States Patent and Trademark Office*